United States Patent
Strauss et al.

(10) Patent No.: US 8,617,192 B2
(45) Date of Patent: Dec. 31, 2013

(54) GUIDE-WIRE SLEEVE FOR FACILITATION OF LESION CROSSING

(76) Inventors: Bradley H. Strauss, Toronto (CA); Thomas C. Waram, Dundas (CA)

( * ) Notice: Subject to any disclaimer, the term of this patent is extended or adjusted under 35 U.S.C. 154(b) by 681 days.

(21) Appl. No.: 12/280,379

(22) PCT Filed: Feb. 22, 2007

(86) PCT No.: PCT/CA2007/000285
§ 371 (c)(1),
(2), (4) Date: Nov. 11, 2008

(87) PCT Pub. No.: WO2007/095751
PCT Pub. Date: Aug. 30, 2007

(65) Prior Publication Data
US 2009/0054875 A1    Feb. 26, 2009

Related U.S. Application Data

(60) Provisional application No. 60/775,327, filed on Feb. 22, 2006.

(51) Int. Cl.
*A61B 17/22* (2006.01)

(52) U.S. Cl.
USPC ................................................. 606/159

(58) Field of Classification Search
USPC ............. 606/110, 113, 114, 127, 128, 159
See application file for complete search history.

(56) References Cited

U.S. PATENT DOCUMENTS

| | | | |
|---|---|---|---|
| 2,944,552 A * | 7/1960 | Cannon | 606/159 |
| 4,776,844 A | 10/1988 | Ueda | |
| 4,898,575 A * | 2/1990 | Fischell et al. | 604/22 |
| 5,078,723 A | 1/1992 | Dance et al. | |
| 5,127,902 A | 7/1992 | Fischell | |
| 6,036,708 A * | 3/2000 | Sciver | 606/159 |
| 6,514,217 B1 | 2/2003 | Selmon et al. | |
| 7,001,369 B2 | 2/2006 | Griffin et al. | |
| 7,540,865 B2 | 6/2009 | Griffin et al. | |
| 7,909,779 B2 * | 3/2011 | Shimogami et al. | 600/585 |
| 2002/0099397 A1 | 7/2002 | Sparks | |
| 2005/0209688 A1 | 9/2005 | Falotico et al. | |
| 2005/0222585 A1 | 10/2005 | Miyata et al. | |
| 2005/0288628 A1 | 12/2005 | Jordan et al. | |

(Continued)

FOREIGN PATENT DOCUMENTS

| CA | 1299953 | 5/1992 |
|---|---|---|
| CA | 2511028 | 12/2005 |

(Continued)

OTHER PUBLICATIONS

Boston Scientific :: Products :: Kinetix™ Guidewire :: Health Care Professionals :: Overv . . . [online] [retrieved Sep. 21, 2010]. Retrieved from the Internet: <URL: http://www.bostonscientific.com/Device.bsci?page=HCP_Overview&navRelId= 1000.100...>. 1 page.

(Continued)

*Primary Examiner* — Ryan Severson
(74) *Attorney, Agent, or Firm* — Nir Lifshitz; Glenn Arnold

(57) ABSTRACT

Flexible sleeve having a leading (distal) edge that can be advanced over a conventional angioplasty guide-wire to facilitate balloon angioplasty catheter and stent catheter crossing complex coronary lesions such as chronic total occlusions or heavily calcified, non-compliant lesions.

28 Claims, 21 Drawing Sheets

(56) References Cited

U.S. PATENT DOCUMENTS

| | | |
|---|---|---|
| 2006/0178653 A1 | 8/2006 | Shimogami et al. |
| 2007/0005084 A1* | 1/2007 | Clague et al. ............... 606/159 |
| 2009/0227983 A1 | 9/2009 | Griffin et al. |

FOREIGN PATENT DOCUMENTS

| | | |
|---|---|---|
| JP | 2004-508096 A | 3/2004 |
| JP | 2005-270658 A | 10/2005 |
| JP | 2005-296078 A | 10/2005 |
| JP | 2006174959 A | 7/2006 |
| US | W09956801 A2 | 11/1999 |
| WO | WO 02/19928 A2 | 3/2002 |
| WO | WO 2005/004965 A2 | 1/2005 |
| WO | WO 2008/006111 A2 | 1/2008 |

OTHER PUBLICATIONS

Spectranetics—Products—Vascular Intervention—Cross Solutions—QuickCross Extreme [online] [retrieved Nov. 9, 2010]. Retrieved from the Internet: <URL: http://www.spectranetics.com/products_VI_crossingSolutions_02_quickCrossExtreme.html>. 2 pages.

Spectranetics—Products—Vascular Intervention—Cross Solutions—QuickCross [online] [retrieved Nov. 9, 2010]. Retrieved from the Internet: <URL: http://www.spectranetics.com/products_VI_crossingSolutions_01_quickCross.html>. 2 pages.

Creganna, Medical Devices, minimally invasive medical technologies, catheters, needles, . . . [online] [retrieved Sep. 21, 2010]. Retrieved from the Internet: <URL: http://creganna.com/menu.aspx?menu=38>. 1 page.

de Swart, J. B. R. M. et al., *A New Technique for Angioplasty of Occluded Coronary Arteries and Bypass Grafts, Not Associated wth Acute Myocardial Infarction*, Catheterization and Cardiovascular Diagnosis, 13, (1987), pp. 419-423.

Smith, L. D. et al., *Use of a Hollow Wire to Facilitate Angioplasty of Occluded Vessels*, Br Heart J, 61, (1989), pp. 326-330.

Quick-Cross Extreme Support Catheter, Braided Support Catheter, Instructions for Use, Spectranetics P003904-00, (accessed Nov. 8, 2010) pp. 1-4.

Quick-Cross Support Catheter, Instructions for Use, Spectranetics, Jun. 2010, pp. 1-8.

Office Action for Japanese Application No. 2008-555590 dated Jan. 30, 2012.

Office Action for Japanese Application No. 2008-555590 dated Jan. 23, 2013.

European Search Report for Application No. EP07710640.9 dated Aug. 16, 2013.

* cited by examiner

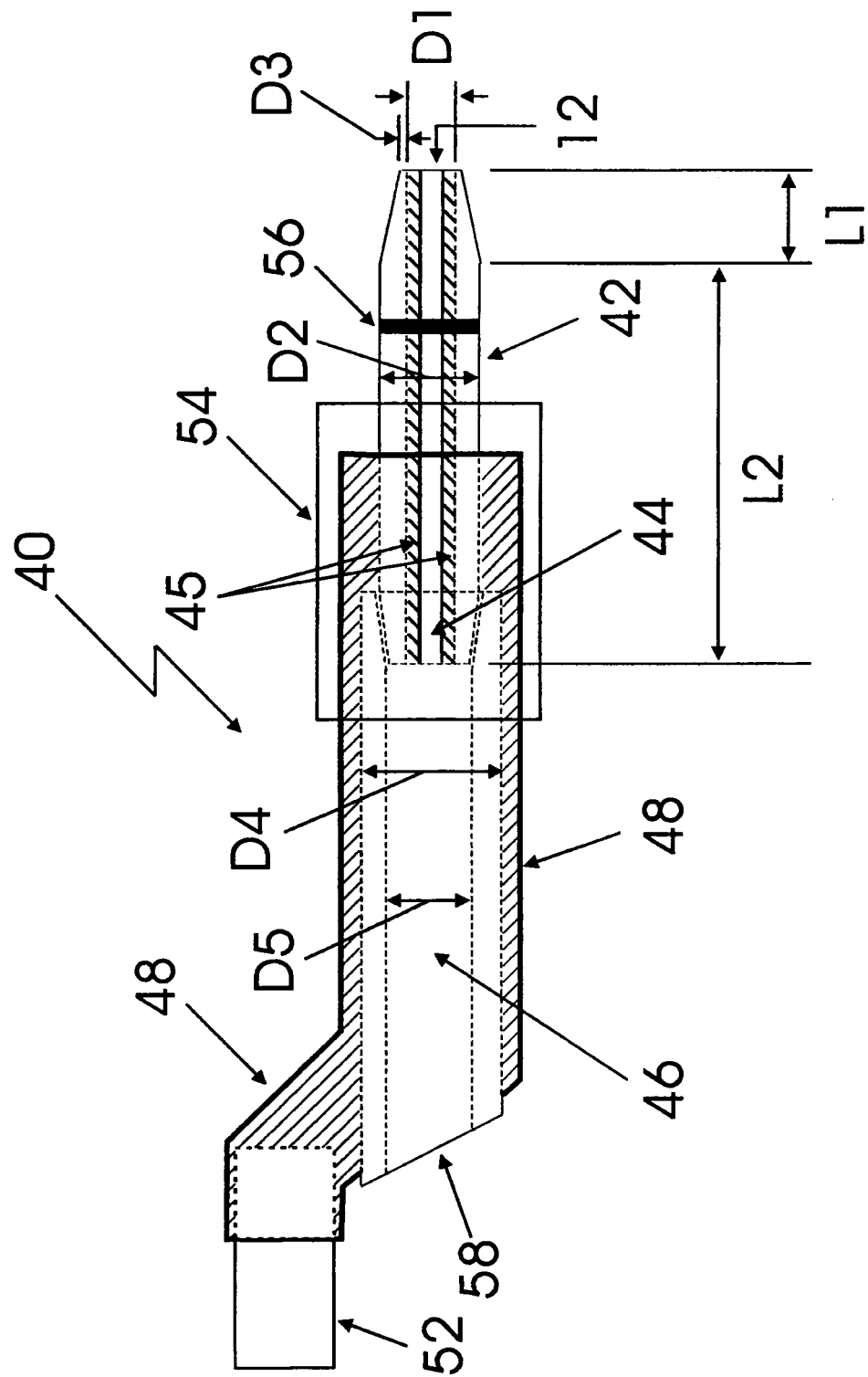

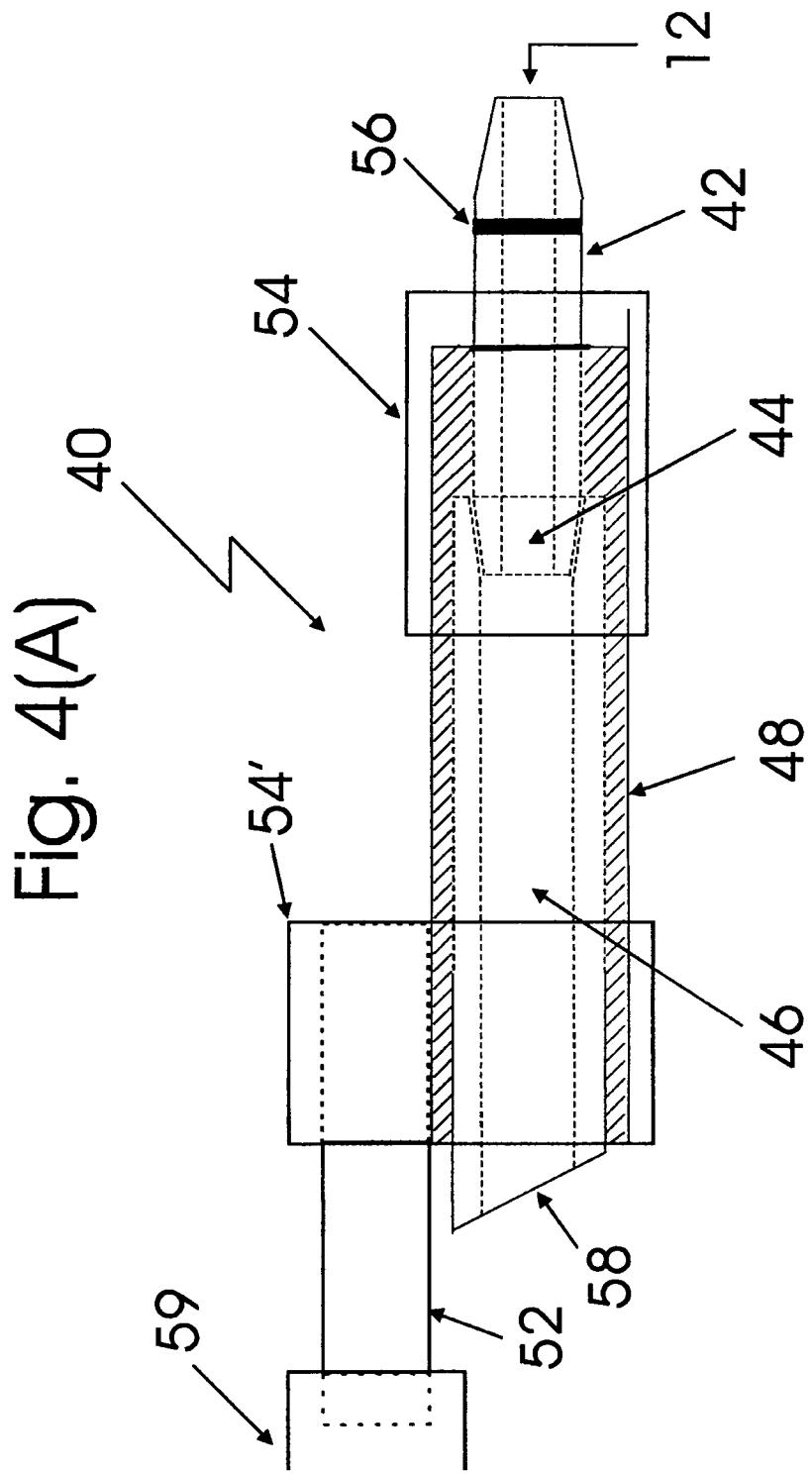

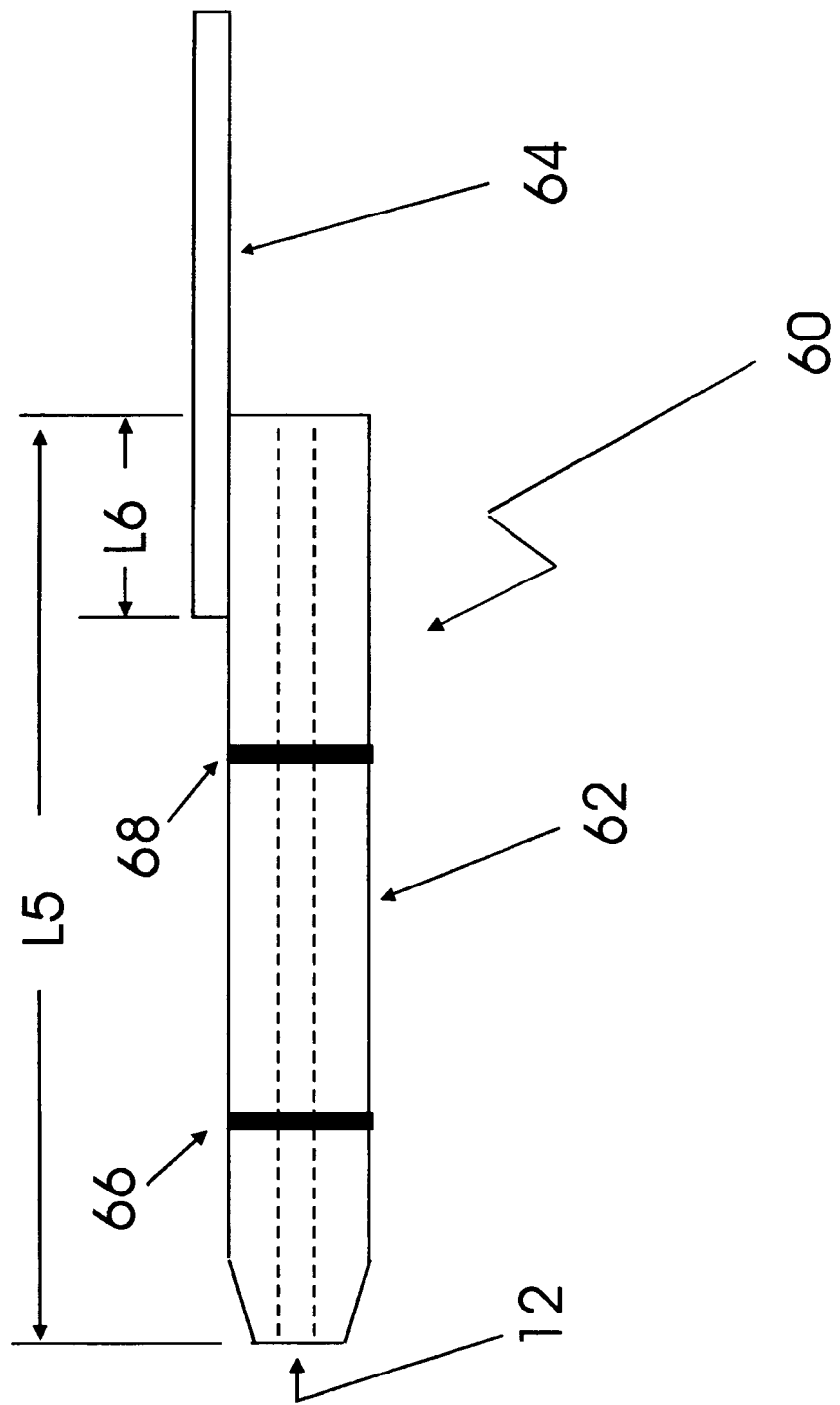

0.022" x0.017" Nitinol tube with 380°C/30min/Air Cool Heat Treatment
3-Point Bend @ 37°C, Bend Span = 14 mm

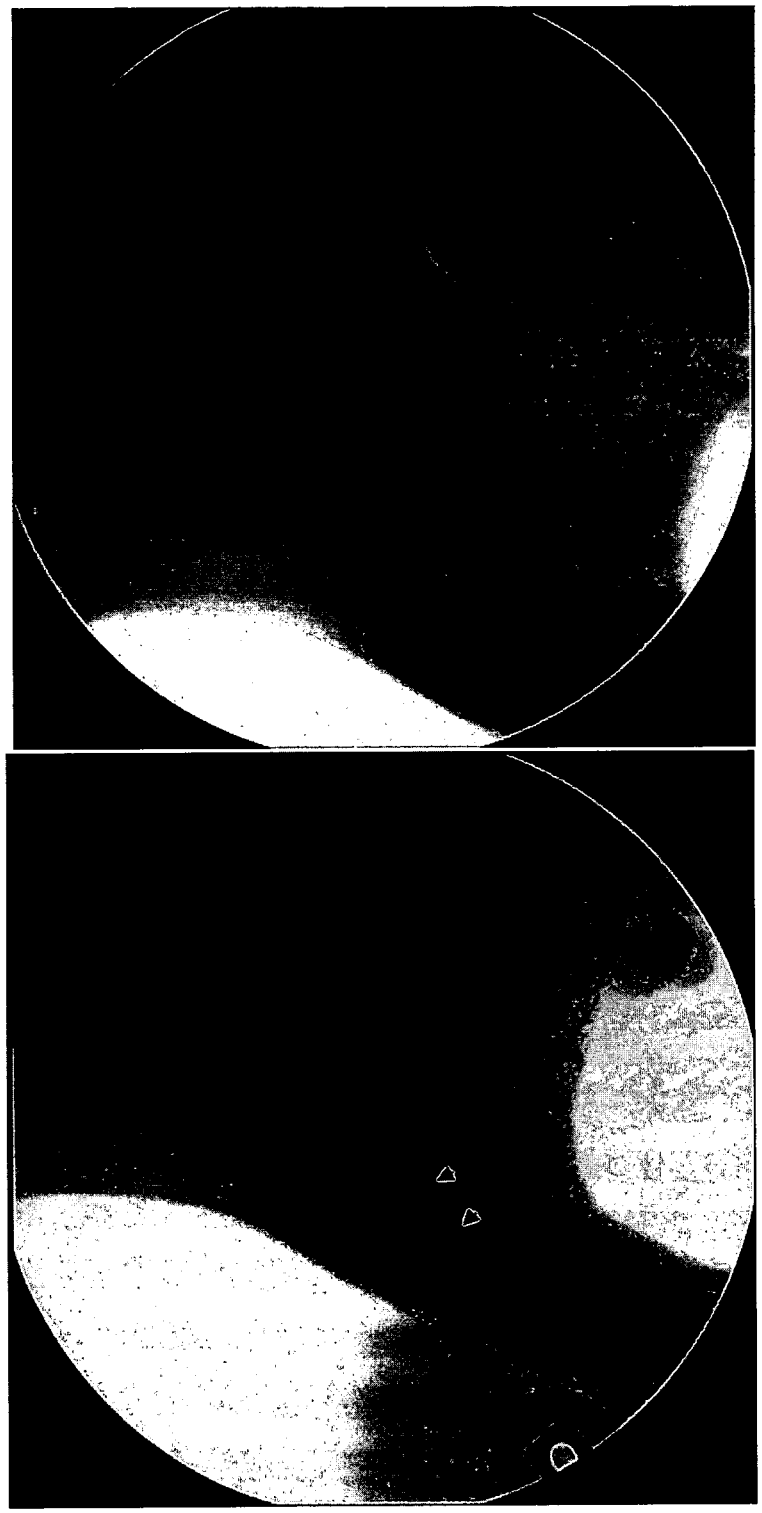

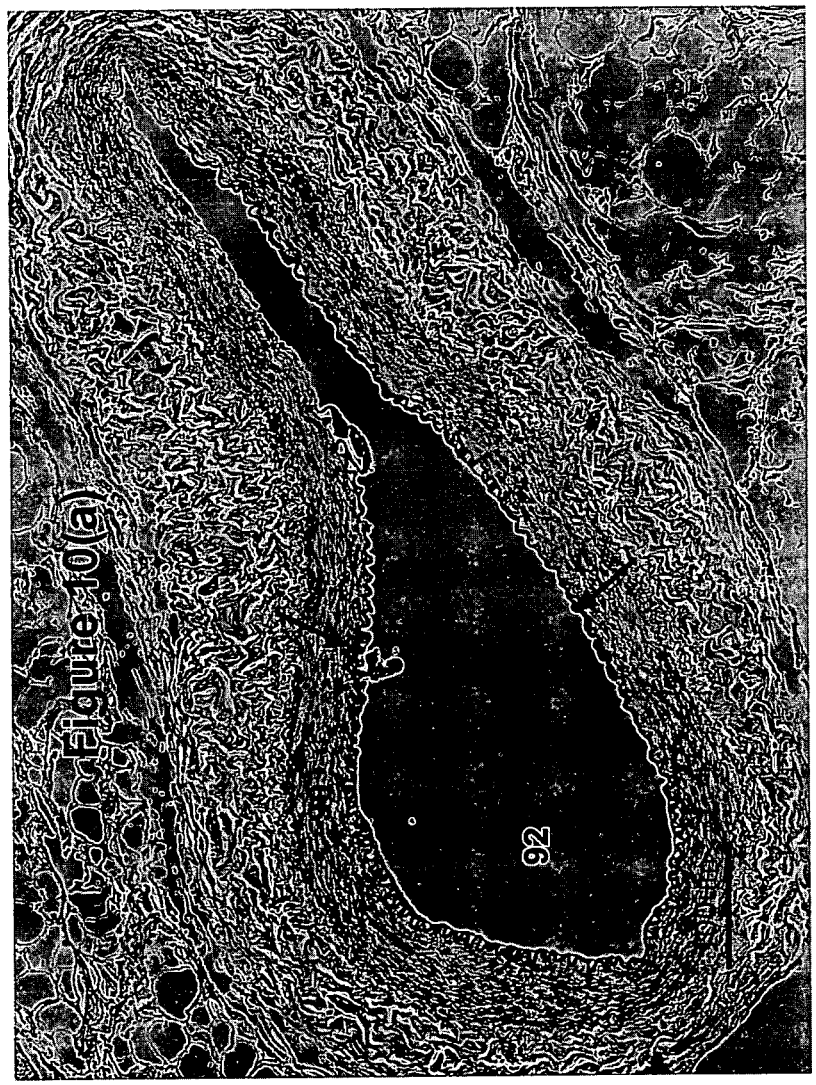

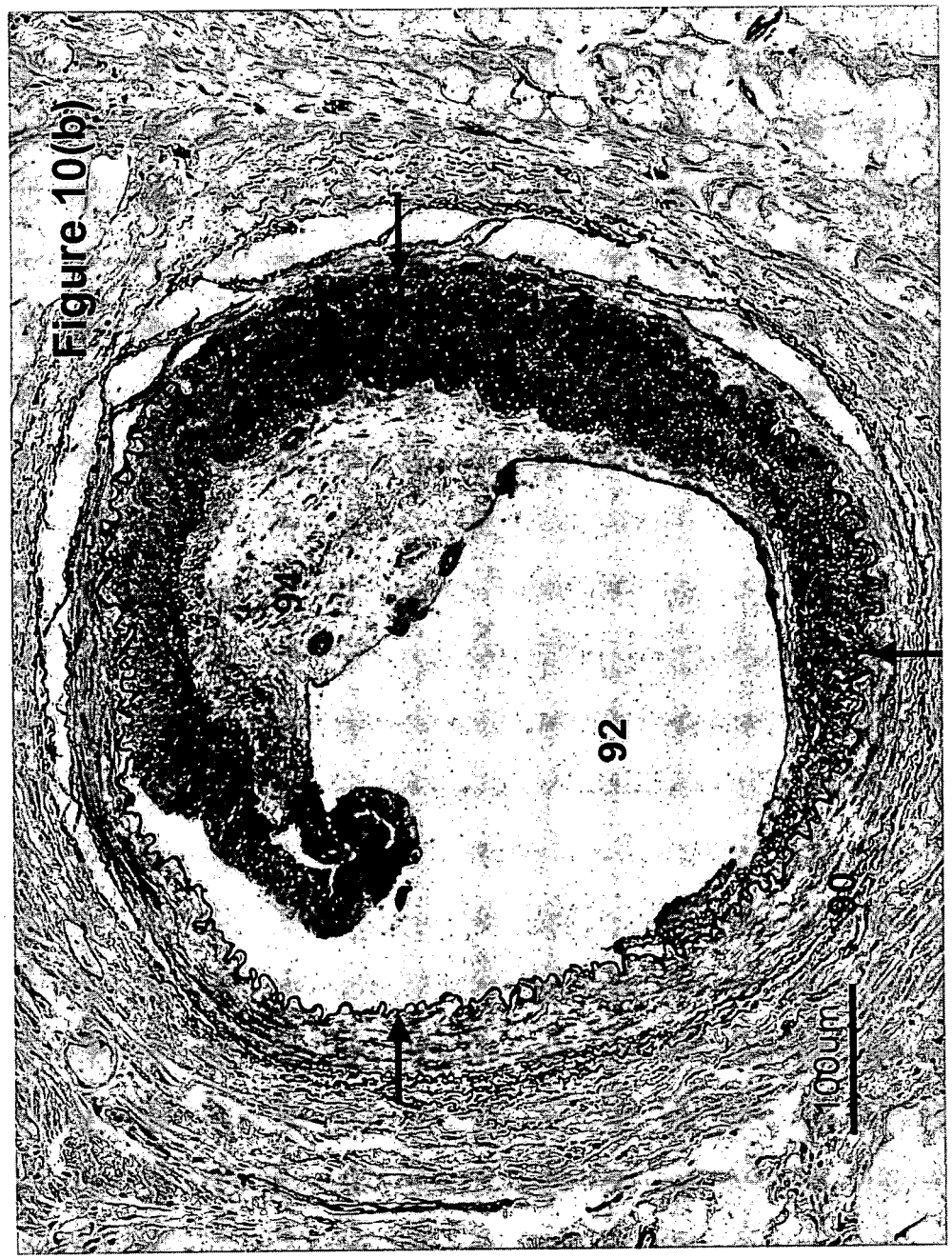

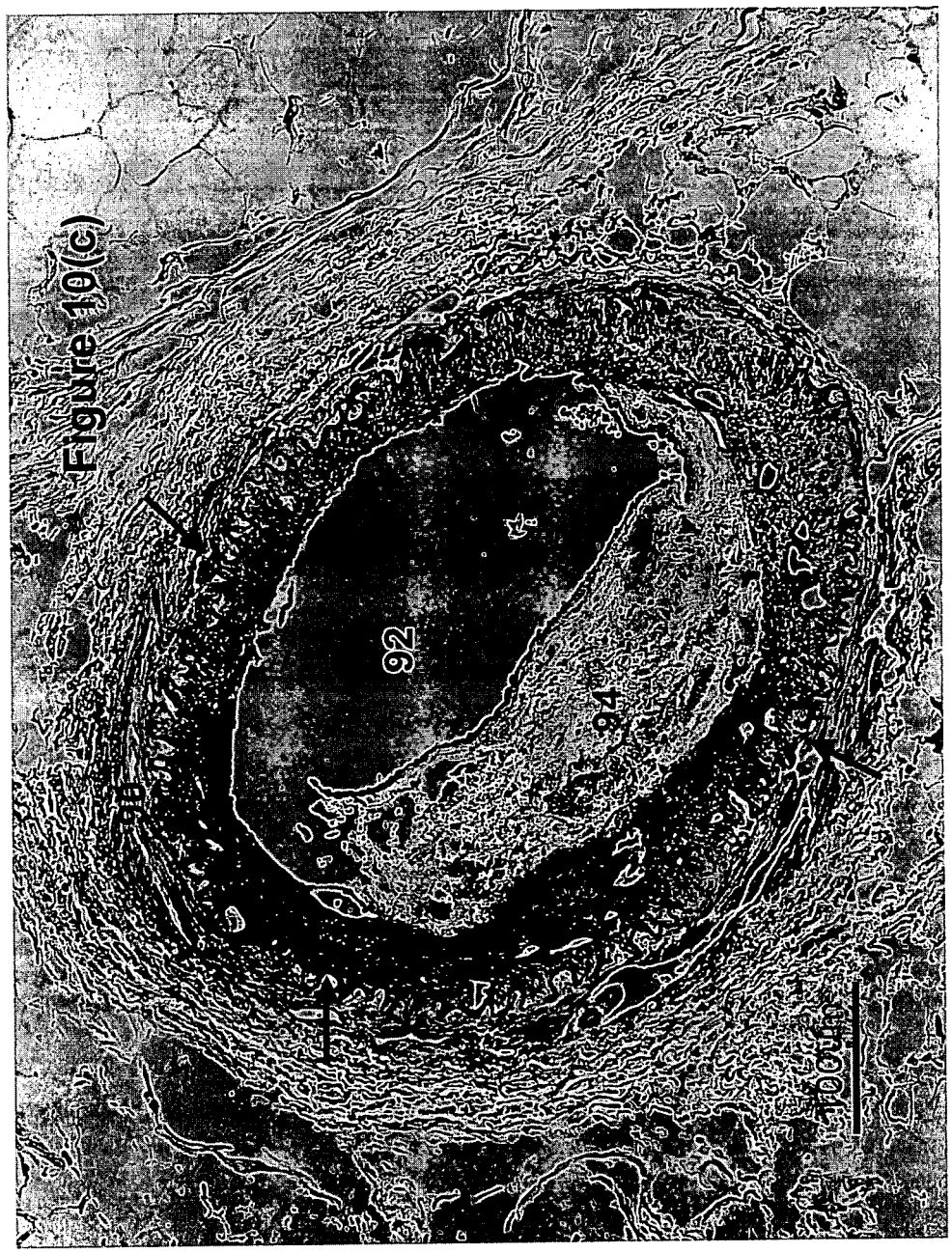

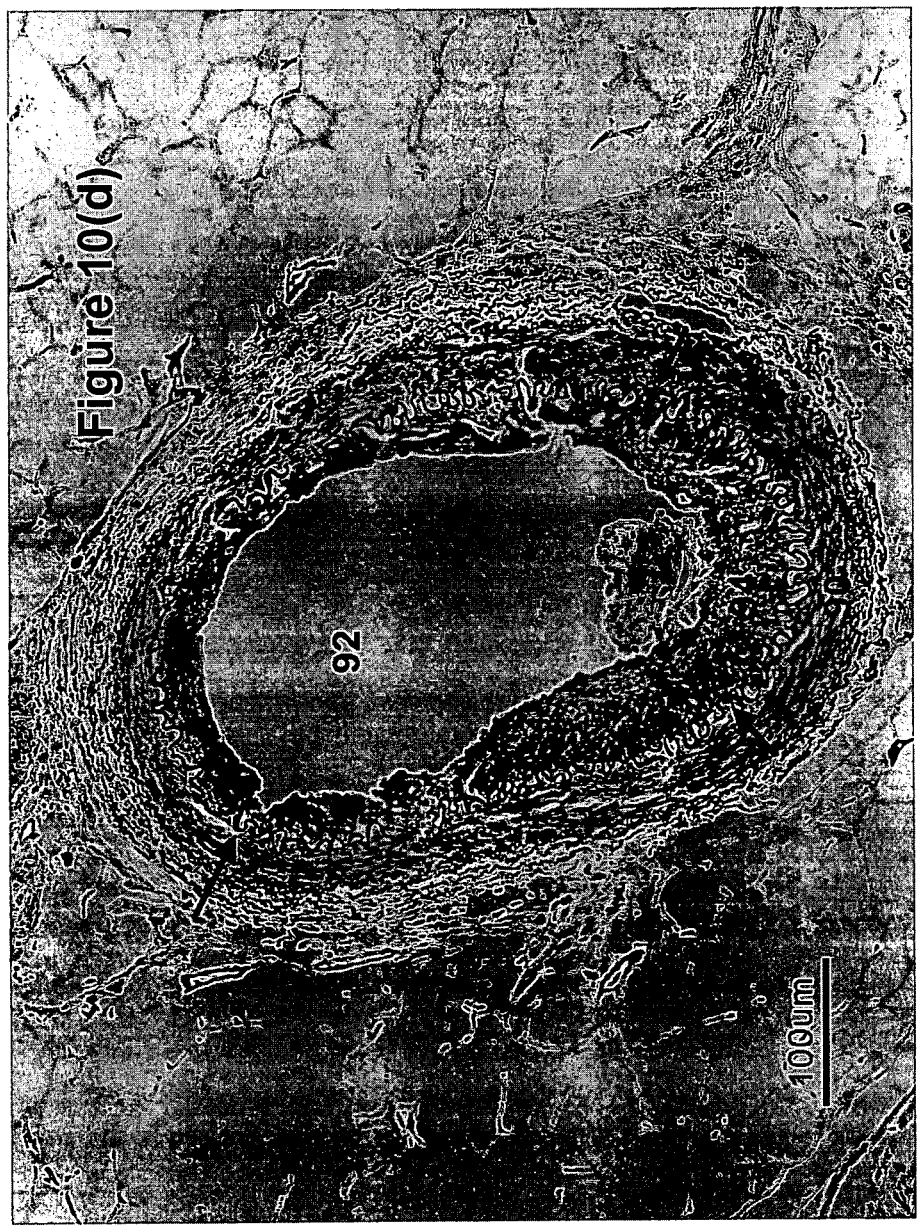

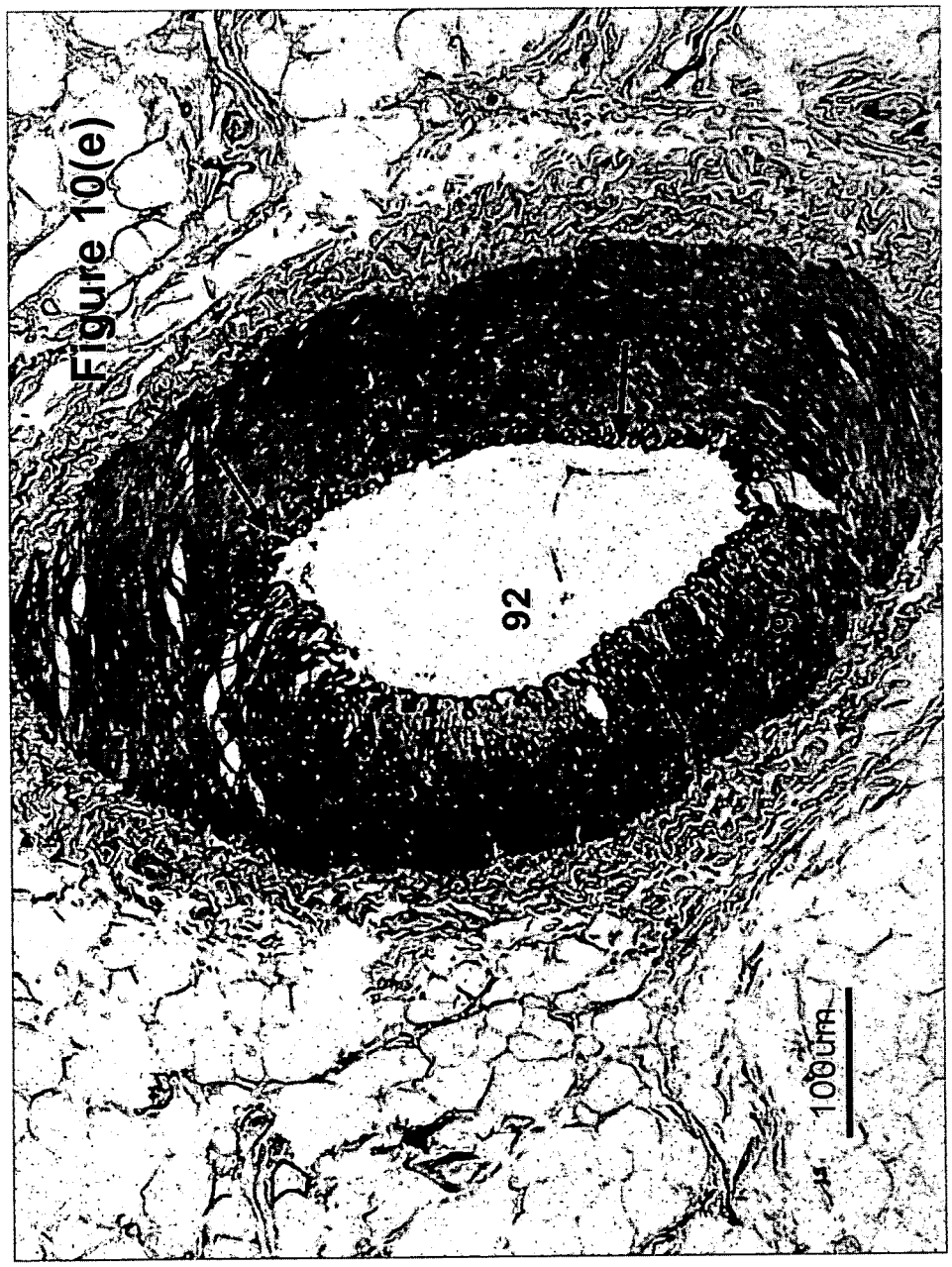

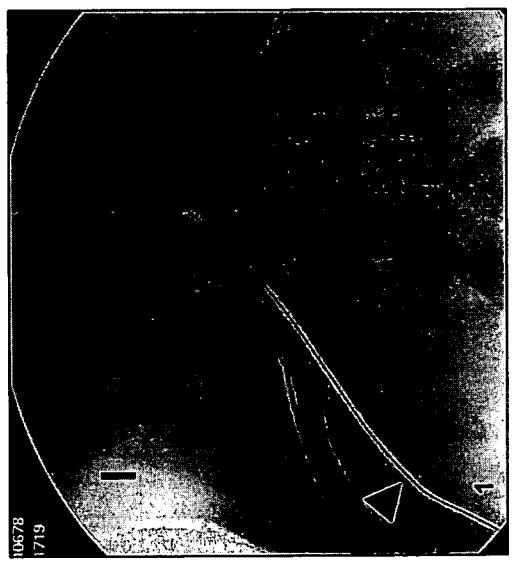
Fig. 11

GUIDE-WIRE SLEEVE FOR FACILITATION OF LESION CROSSING

CROSS REFERENCE TO RELATED APPLICATIONS

This application is a 35 U.S.C. 371 national phase application of International Application No. PCT/CA2007/000285, filed Feb. 22, 2007, which International Application was published by the International Bureau in English on Aug. 30, 2007, and claims priority to U.S. Provisional Application No. 60/775,327, filed Feb. 22, 2006, both of which are incorporated herein by reference in their entirety.

FIELD OF THE INVENTION

The present invention is in the field of animal vessel repair, such as balloon angioplasty, that includes passage of a guide-wire-mounted device through a narrowed vessel and expansion of the narrowed vessel.

BACKGROUND OF THE INVENTION

Coronary artery disease is a leading cause of mortality in the western world. Percutaneous coronary interventions (PCI) are a current mainstay of therapy. In 2001, an estimated 1.051 million PCI were performed in the United States (1). Procedural success rates in stenotic (but non-occluded) coronary artery lesions are in excess of 95%. However, in selected lesion subgroups, such as chronic total occlusions (CTO), calcified stenosis and non-compliant plaques, procedural success rates are considerably lower. In CTO, success rates are in the range of 60 to 70% range (2-4), despite continuing improvements in angioplasty technology (5,6). This current success rate for CTO may even be an overestimation, since a significant portion of CTO crossings are not attempted due to low expectation of success. Inability to cross the CTO with a guide-wire is responsible for 75% of PCI failures (4,7). In certain cases, the balloon or stent cannot cross the lesion despite successful guide-wire crossing.

A chronic total occlusion is an occlusion that is greater than a month old. CTOs are commonly found in patients undergoing diagnostic coronary artery catheterisation with up to 20-33% of patients reported to have one or more CTO (8,9). This includes a large number of patients that have not experienced myocardial infarction. Successful revascularization of a CTO significantly improves angina in symptomatic patients (10,11) and more recent data suggest improvement in left ventricular function (12-16), and even in reduction of mortality (17-19). Currently, there are two major therapeutic strategies for addressing problems associated with CTOs: coronary artery bypass graft surgery (CABG) or percutaneous coronary interventions (angioplasty or stenting). Angioplasty includes placement of a small (360 µm diameter) guide-wire through the tissue obstructing the lumen in a CTO in order to reach the distal arterial lumen. The technical difficulty of performing PCI in CTO, primarily because of inability to cross CTO with a guide-wire, is reflected in the low rates of PCI for CTO (accounts for less than 8% of all PCI), despite the benefits of a positive outcome (20). Since PCI have severe limitations in this patient subset, clinicians frequently decide to refer these patients for CABG or persist with (often ineffective) medical therapy. The presence of one or more CTO in vessels supplying viable myocardium remains one of the most common reasons for referral for CABG rather than attempting PCI (21).

Several lesion characteristics have been identified as predictors of procedural success and influence the decision to proceed with angioplasty. Duration of occlusion, which is often difficult to ascertain, is a major predictor. Recent coronary occlusions, i.e. less than three months old, are successfully dilated 74%-89% (4, 22) of the time. However, success rates in occlusions greater than three months old decline to 45%-59%. Other predictors of procedural failure include occlusion length (greater than 15 mm) (6,7,9), presence of bridging collaterals, and an absence of a tapered funnel leading into the occluded segment (23). Failure rates are also higher in absolute occlusions (no distal opacification) than in functional total occlusions (subtotal occlusion with faint late anterograde opacification of the distal segment without discernible continuity) (9,24,25).

Inability to cross the CTO with a guide-wire is responsible for 75% of PCI failures (4,7). In some cases, the balloon or stent cannot cross the lesion despite successful guide-wire crossing.

Successful angioplasty requires that the operator first place a small (0.014" or 360 µm diameter) guide-wire through the narrowed lumen of a lesion in order to reach the distal arterial lumen. This is followed by placing a balloon angioplasty catheter or coronary stent mounted on a balloon catheter across the lesion, then dilating the balloon to expand the lesion or deploy the stent. The cross-sectional size of balloon angioplasty catheters varies. A fixed-wire balloon catheter, e.g. ACE, Boston Scientific, typically has a diameter of about 610 µm. A rapid exchange balloon, e.g. Maestro balloon-check 1.5 mm balloon, typically has a 900 µm diameter. Over-the-wire (OTW) balloon catheters typically have a 1100 µm diameter, e.g., Opensail of Guidant Corp. There are different strategies to overcome this limitation. Recently it has been reported that a 0.9 mm high-energy excimer pulsed laser catheter (X80, Spectranetics, Colorado Springs, Colo.) had a success rate of 92% in crossing calcified and/or balloon-resistant lesions that could not be crossed with a 1.5 mm diameter balloon catheter (26,27). However, the laser system is expensive and access is limited to a few clinical sites. Rotational atherectomy has also been used in such situations but first requires crossing the lesion with a rota-wire, which is more difficult to manipulate than conventional guide-wires, particularly in a chronic total occlusion.

The underlying atherosclerotic plaques in chronic total occlusions are predominantly fibrocalcific (28), consisting of smooth muscle cells, extracellular matrix, calcium and variable amounts of intracellular and extracellular lipids (29). Inflammatory cells are commonly seen (28). Collagens are the major structural components of the extracellular matrix, comprising up to 50% of the dry weight (30,31), with predominance of types I and II (and minor amounts of IV, V and VI) in the fibrous stroma of atherosclerotic plaques (32,33). In CTO less than 1 year old, proteoglycans are also commonly found in the intima. Thrombus formation contributes to a varying degree, depending on the severity of the underlying atherosclerotic plaque, and can result in single or multiple layers of clot. Over time, this thrombus becomes organized and converted into a collagen-rich fibrous tissue (known as intimal hyperplasia), which eventually is incorporated into the underlying atherosclerotic plaque (29). Older, more organized collagen-rich fibrous tissue, particularly with high calcium content, appears to be the barrier to successful crossing with current angioplasty techniques of both the guide-wire and the balloon angioplasty or stent catheter. In severely stenosed but non-occluded arterial lesions, particularly if heavily calcified and fibrotic, operators also may encounter difficulties in crossing the balloon angioplasty or stent catheters, even when the guide-wire has successfully crossed.

The literature contains descriptions of a penetration catheter (Tornus, Sahi Intecc, Aichi, Japan) (34). The Tornus catheter consists of a three parts: the main shaft with surface coating, the polymer sleeve and a hub connector. The main shaft is a coreless, stainless steel coil that is right-handed lay (clockwise). Eight stainless wires are stranded in the coil. The outside diameter is 0.70 mm. The inside diameter is 0.46 mm and is suitable for the 0.014" guide-wire. The device is advanced across severe stenosis by rotating the guide-wire counterclockwise rotation, the shaft being stranded clockwise. The profile of the tip is 0.62 mm in diameter and it is made of stainless-platinum alloy. Tsuchikane et al. have described the initial use of this device in patients with severe coronary artery disease or calcified stenosis when a 1.5 mm balloon catheter or microcatheter did not cross through the lesion after successful wire crossing. In 14 patients, the Tornus was successfully crossed through all lesions without distal embolism, coronary perforation or dissection. Stent implantation was successfully performed in all 14 patients.

In summary, percutaneous coronary interventions are an important form of coronary artery revascularization therapy. In most cases, crossing the lesion with guide-wires and angioplasty and stent catheters is quite straightforward. However, in a particular subgroup of coronary lesions, e.g., chronic total occlusions or heavily calcified, non-compliant stenoses, crossings with balloon angioplasty catheters and stent catheters remain a challenge despite successful crossing with a guide-wire.

There is thus a need to be able to treat lesions to facilitate balloon angioplasty or stent catheter passage across an arterial occlusion or stenosis after the guide-wire has successfully crossed.

SUMMARY OF THE INVENTION

The present invention provides a treatment for a mammalian vessel, including a device for providing such treatment. The vessel, for example, and artery contains an Occlusion, a narrowing, or some obstruction which is crossable by a guide-wire, but which needs widening. Subsequent to widening, for example, it may become possible to cross the site to be treated with a balloon catheter for angioplasty, or to install a stent.

In one embodiment, the invention is a device for treatment of a mammalian vessel having an occlusion crossable by the guide-wire of a balloon catheter. The device includes a hollow sleeve having a distal end and a proximal end, and a lumen for receipt of the guide-wire therethrough. The distal end of the sleeve has a leading edge that is shaped to cut away surrounding portions of the occlusion crossed by the guide-wire as the sleeve is advanced over the wire and through the occlusion.

The sleeve may or may not be accompanied with the guide wire with which it is to be used.

The leading edge of the sleeve presents a cutting edge radially spaced from the center of the lumen of the sleeve. It is possible for the cutting edge to be serrated.

In certain embodiments, the sleeve has a surface which slopes outwardly from the cutting edge. Such a surface would generally follow behind (be upstream of) the leading edge and operate as a wedge to spread apart an occlusion as the sleeve is advanced therethrough.

The sloped surface, which can have the shape of a truncated cone, often extends from the leading edge to a location up to about 0.300 or up to 0.250 or up to 0.200 or up to 0.15 inches upstream of the leading edge. The location is usually at least 0.05 inches upstream of the leading edge, often between 0.05 and 0.15 inches upstream of the leading edge. In an embodiment disclosed herein a canted surface extends to a location that is about 0.1 inches upstream of the leading edge.

The cutting edge itself can be arcuate. That is, when the sleeve is viewed head on (from a point downstream of the leading, or distal end) the cutting edge appears much like a curved line, and preferably a circle.

The lumen of the sleeve would usually have a maximum diameter of 0.03 inches.

The radial distance between the surface of the lumen and the outer surface of the sleeve would usually be between 0.004 and 0.009 inches, more typically between 0.004 and 0.007 inches, and more often between 0.005 and 0.007 inches, typically 0.006 or 0.007 inches.

The cross-section of the sleeve is often in the shape of an annulus, which means if the wall of the sleeve is taken in cross-section its outer and inner walls appear as concentric circles.

The sleeve is preferably composed of a flexible metal, especially at the leading end, or cutting end.

A metal that has been found in feasibility studies to be useful is a superelastic metal, a term known in the industry and described in greater detail below. In conjunction with such property, a measure of the flexibility of such a metal is its $A_f$ temperature. An $A_f$ temperature of between about 35° C. and 45° C., or between 36° C. and 44° C., or between 36° C. and 43° C., or between 37° C. and 42° C. is possible according to particular embodiments of the invention, with an $A_f$ temperature in the lower half of the 35° C. and 45° C. range likely to be found closer to optimal.

The metal can be selected from the group of nickel-titanium (nitinol) alloy, stainless steel, an alloy of cobalt, chromium, nickel and molybdenum (Elgiloy), an alloy of titanium, and combinations thereof. The metal of sleeves of the disclosed embodiments is nitinol.

The device can be used with an over-the-wire (OTW) delivery system, or a monorail delivery system. In the case of an OTW system, the sleeve will be much longer than in the case of a monorail system. So a sleeve of the invention can be anywhere from about 2 cm up to about 150 cm. In the case of a monorail system, the sleeve length will be in the lower end of the range, more likely no more than about 20 cm. A sleeve length of between about 5 cm and 15 cm is likely to be very common.

A device of the invention can further include a hollow sheath secured at a proximal end (i.e. at the upstream end) of the sleeve. Such a sheath has a central passage extending through it, in communication with the lumen of the sleeve to permit passage of the guide-wire through the sheath-sleeve combination. The sheath would generally be of a different material from the sleeve, for example, a synthetic polymeric and it would likely be more flexible than the sleeve.

The combined length of the sleeve and sheath can be of any suitable length, typically up to about 40 cm. If for use with a monorail delivery system, the sheath-sleeve would further include a pusher wire, which would be connected at the proximal end of the sheath. The pusher wire is used by the surgeon to push the device along the guide-wire to an e.g., arterial occlusion.

A sleeve can also include means for reducing friction between its inner lumen surface and the guide-wire. Such means can include a low-friction coating. Such a coating could be a parylene polymer, and specifically as described in a particular embodiment herein, parylene C. A parylene polymer would most often be applied the sleeve lumen surface by vapor deposition.

To assist the surgeon in manipulating a device of the invention, the sleeve can include at least one radio-opaque marker.

In another embodiment, the invention is a device for treatment of a human artery having an occlusion crossable by the guide-wire of a balloon catheter. The device includes a hollow sleeve having a distal end and a proximal end, and a lumen for receipt of the guide-wire therethrough. The distal end of the sleeve provides a leading edge that is shaped to shave off surrounding portions of a said occlusion as the sleeve progresses through the occlusion crossed by the guide-wire.

In a particular aspect of this device, the sleeve has a wall defined between the inner surface of the lumen and an outer surface of the sleeve. The wall has an average thickness no greater than 0.006 inches; the lumen has an inner diameter of between 0.016 and 0.018 inches; the outer diameter of the sleeve is between 0.022 and 0.024 inches, the sleeve has a length of no more than 20 mm; and the sleeve is of nitinol or of a nickel-titanium-copper alloy.

In another aspect, the sleeve is of unitary construction and includes an outer sidewall having a surface which cants outwardly from the leading edge, wherein the surface area of the outer canted surface makes up less than 10 percent of the total surface area of the outer sidewall.

In yet another aspect, the leading edge, i.e., the cutting edge of the sleeve has a thickness of no more than about 0.002 inches, preferably no more than about 0.001 inches.

In a preferred aspect, the leading edge is the only cutting edge of the sleeve, the remainder of the device presenting smooth surfaces relatively free of protuberances, cutting edges, etc. to facilitate advancement of the sleeve through an artery.

In a particular device, the sidewall is of constant cross-section for at least 85 percent of its length, preferably at least 90 percent of its length.

In a device in which the sleeve is a metal of nitinol or of a nickel-titanium-copper alloy, the metal has an $A_f$ temperature of between about 35° C. and 45° C., or between 36° C. and 44° C., or between 36° C. and 43° C., or between 37° C. and 42° C.

The device can include a the guide-wire detachably affixed, or integrally affixed to the sleeve, even if, as in certain illustrated embodiments, not directly connected to the sleeve.

The invention includes a method for treating chronically occluded animal tubes and cavities. The first step in the method is crossing the occluded animal tube with a guide-wire. There follows the advancement over the guide-wire of a flexible sleeve having a leading cutting edge to shave off a superficial layer of tissue of the occlusion or otherwise narrowed vessel. The flexible sleeve will then be withdrawn and followed by installation of an angioplasty balloon catheter or stent catheter. If necessary, progressively larger sleeves will be advanced across the stenosis until it is possible to cross the lesion with the balloon angioplasty catheter or stent catheter.

The sleeve can include a a tapered distal tip that will function to stretch the stenosis slightly as the sleeve is advanced therethrough.

In another aspect, the invention is a method of treating a crossable occlusion of an artery. The method includes crossing the occlusion with a guide-wire followed by inserting a sleeve mounted on the guide-wire and having a leading cutting edge through the occlusion to shave a portion off a portion of the occlusion.

The sleeve can be any of the sleeves described in this specification.

A method of the invention can be of preparing a crossable occlusion for balloon angioplasty. Such method includes (a) crossing the occlusion by inserting a guide-wire of a catheter delivery system through a passage of the occlusion; (b) mounting a first sleeve of the invention onto the guide-wire; (c) delivering the sleeve to the proximal end of the occlusion; and (d) pushing the sleeve along the guide-wire through the occlusion so as to shave off at least a portion of the occlusion so as to increase the diameter of the passage of the occlusion.

In another aspect, the invention is a method of preparing a crossable arterial occlusion for balloon angioplasty which includes (a) crossing the occlusion by inserting a guide-wire of a monorail delivery system through a passage of the occlusion; (b) mounting a first sleeve suitably dimensioned for use in a monorail delivery system onto the guide-wire; (c) delivering the sleeve to the proximal end of the occlusion; and (d) pushing the sleeve along the guide-wire through the occlusion so as to shave off at least a portion of the occlusion so as to increase the diameter of the passage of the occlusion.

According to this method, the first sleeve can have a cutting edge radially spaced a first distance from the center of the lumen, and additional steps include (e) removing the sleeve from the guide-wire; (f) mounting onto the guide-wire a second sleeve wherein, the second sleeve has a cutting edge radially spaced a second distance from the center of the lumen thereof, and the second distance is greater than the first distance; and (g) repeating steps (c) and (d).

The invention includes a method of manufacturing a device for augmenting intraluminal diameter of an occlusion of a mammal, the method including:
  providing a guide-wire;
  providing a sleeve of the invention;
  disinfecting the wire and sleeve; and
  packaging the sleeve and guide-wire in a hermetically sealed package.

The best mode of the invention as currently known to the inventor is described below, while broader aspects of the invention are included in the claims which follow thereafter.

BRIEF DESCRIPTION OF THE DRAWINGS

FIGS. 4 and 4(a) show a third embodiment prototype sleeve of the invention installed at the distal delivery end of a guide-wire catheter tube for use with a monorail delivery system;

FIG. 5 shows a fourth embodiment sleeve for use with a monorail delivery system;

FIG. 9(e) shows a balloon advanced along the guide-wire across the occlusion subsequent to treatment of the occlusion, the distal end of the balloon highlighted by the radio-opaque dot indicated by the arrow;

FIG. 9(f) is an angiogram obtained after removal of the balloon and guide-wire;

FIGS. 10(a)-(e) show the histology of the chronic total occluded femoral artery of the second feasibility study after crossing with the guide-wire, the sleeve, and the angioplasty balloon catheter. FIG. 10(a) is of the femoral artery immediately proximal to the occlusion. FIGS. 10(b), (c) and (d) are of the proximal, mid and distal parts of the occluded artery, respectively, and FIG. 10(e) is of the femoral artery immediately distal to the occlusion. The internal elastic lamina is indicated by arrows. Within the occlusion, the lumen is patent as a result of the passage of the guide-wire and angioplasty balloon therethrough. There is no apparent damage to the medial layer of the vessel wall as a result of the procedure;

DETAILED DESCRIPTION OF THE INVENTION AND PREFERRED EMBODIMENT(S)

The present invention provides a device expected to improve the procedural results of balloon angioplasty catheter or stent catheter crossings across complicated lesions such as heavily calcified lesions. A device of the present invention finds use in treating occlusions that can be crossed by a guide-wire having an outer diameter of e.g. 0.014 inches, but where treatment would be improved by a widening of the passage through the occlusion. In the context of this invention, the occlusion is thus referred to as a "crossable occlusion".

Figure 1:
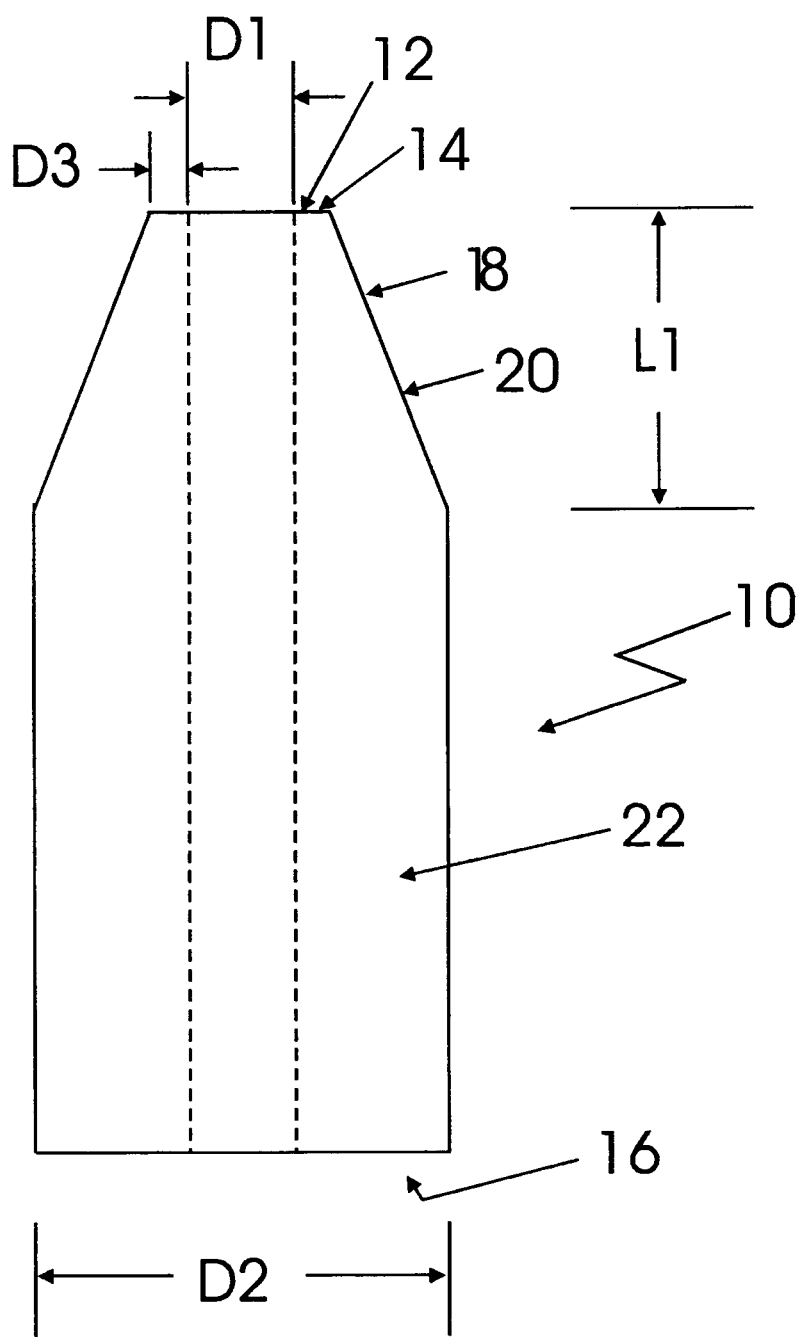
FIG. 1 illustrates a first embodiment sleeve of the present invention in cross section.
Figure 2A:
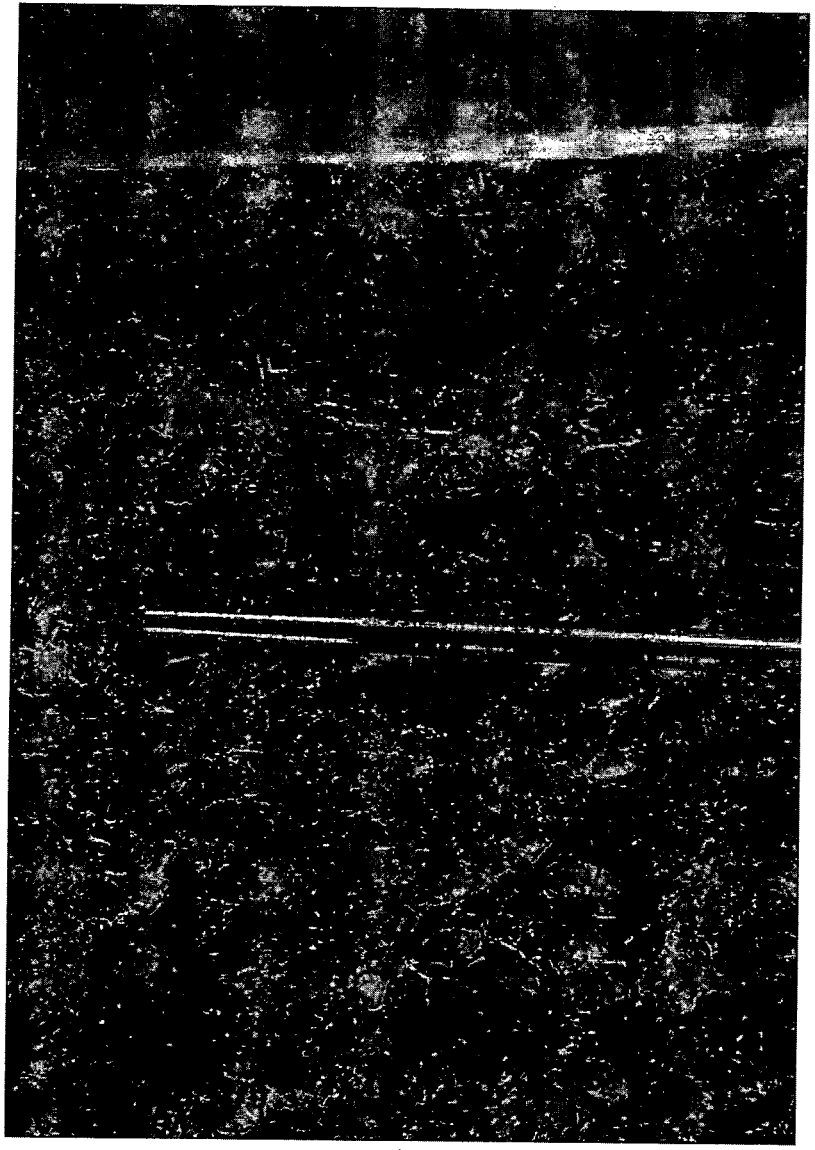
FIG. 2(a) is a photograph showing a side of the first embodiment prototype sleeve of the invention.
Figure 2B:
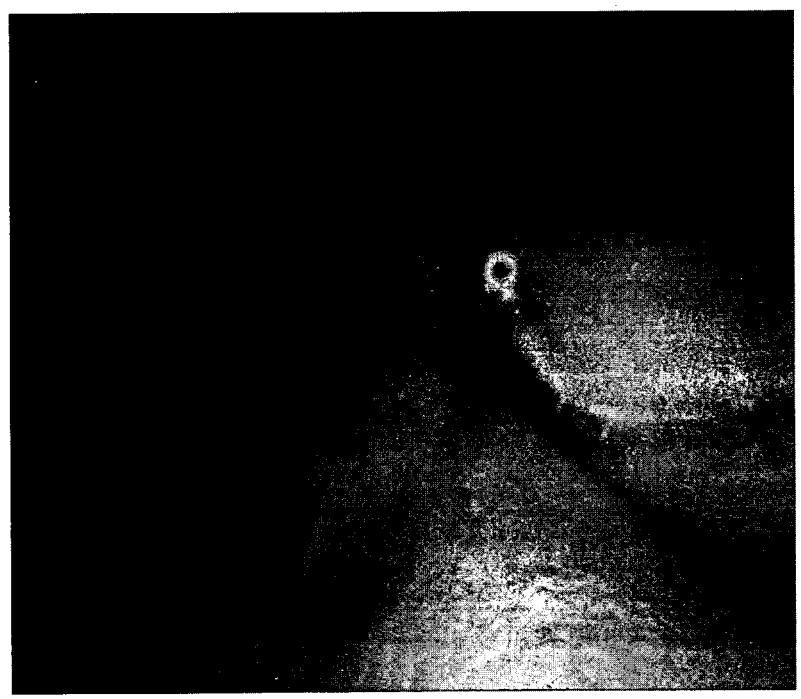
FIG. 2(b) is a photograph showing an end view of the tip of the first embodiment prototype sleeve.

Turning to the figures, a first embodiment device is shown in FIGS. 1 and 2. The device includes a flexible sleeve 10 having at its distal end 12 leading edge 14. The cross-sectional diameter of the distal end increases running from the lead edge towards the proximal end 16 to form tapered section 18. The outer surface 20 cants radially outwardly moving towards the proximal end of the sleeve. The length, L1, of the leading tapered portion is 0.100 inches while the inner diameter, D1, of the hollow portion of the sleeve is 0.015 inches. The outer diameter of the tip section 18 thus decreases towards the distal end of the tip. The distal section of the sleeve has tapered distal tip with a proximal section 22 of constant outer diameter upstream of the tip section. The outer diameter D2 is 0.021 inches. Leading edge 14 of the sleeve presents cutting edge having thickness D3 of 0.001 inches. It is also possible to include another tapered section upstream of section 22 such that the diameter of the sleeve decreases towards the proximal end. This in turn can be followed by a section of reduced constant diameter proximal to the tapered section so as to increase the overall flexibility of the sleeve. The first embodiment sleeve is for use with an over-the-wire (OTW) delivery system and has an overall length appropriate for its intended use, e.g., about 55 inches.

In use, a guide-wire is installed in the artery and passed through the lesion to be treated. The tapered distal tip of the sleeve is advanced over the guide-wire and is itself advanced across the lesion. This device will both stretch the lesion and shave superficial material of the obstructive lesion to improve the compliance of the lesion in subsequent operations, e.g. balloon crossing or stent installation. The sleeve may be used e.g., in a severely narrowed artery that is not completely occluded but where there is difficulty in advancing an angioplasty balloon catheter across the lesion. In addition, the sleeve may also be used after placement of the guide-wire to enlarge the channel in the narrowed artery, i.e., stenosis, so that a stent can be positioned across the stenosis. This may be done after dilatation with an angioplasty balloon catheter or possibly as an alternative to a dilatation with an angioplasty balloon catheter.

Although this device has been developed for use in coronary arteries, it can also be used in other sites in a mammalian, particularly human body where there are narrowings such as peripheral arteries, e.g., iliac, femoral or popliteal arteries, renal arteries, carotid arteries, vertebral arteries, or other narrowed tube-like structures such as ureters, fallopian tubes, bile ducts or narrowed arterial-venous grafts or fistulae.

The shaft of the sleeve is constructed of, for example, nickel-titanium alloy, nitinol. The inner diameter is generally larger than the outer diameter of a conventional guide-wire (0.014 inches), with which it is typically to be used, so as to readily accommodate receipt of the guide-wire therethrough. The smallest inner diameter of the smallest sleeve is thus about 0.015-0.018 inches with an outer diameter of 0.021-0.024 inches. Larger sleeves that would progressively dilate the channel could also be used. The inner diameter of the larger sleeves can be, for example, 0.020", 0.025" and 0.030". The corresponding outer diameter would be 0.026", 0.031", 0.036". Alternatively, part or all of the shaft could be provided by a shaft composed of a polymer or composite material similar to one used in angioplasty balloon catheters with only the tip made of a metal or alloy such as nitinol, stainless steel, a cobalt-chromium-molybdenum alloy, a cobalt-chromiummolybdenum-nickel alloy (Elgiloy), a titanium alloy or some other metal or alloy. In a preferred sleeve, the leading end is adapted for use with any conventional guide-wire of suitable diameter, including coated and non-coated wires.

The sleeve is hollow having a center port running therethrough, i.e. the device is tube-like having a central passage sufficiently large to accept a 0.014 inch (diameter) angioplasty guide-wire therethrough. The prototype devices used in the Studies 1 and 2 described herein had a 0.021 inch outer diameter and 0.015 inch inner diameter. It is thought that more optimal dimensions may be a 0.024" outer diameter and a 0.017" inner diameter.

Disadvantageously, there is friction between the guide-wire and the inner surface of the guide-wire port or lumen of the sleeve as the sleeve moves over the wire, as has been experienced with certain coated guide-wires such as the Choice PT (Boston Scientific, Natick, Mass., U.S.A.). This problem manifests itself, for example, by stripping of some of the coating from the wire. This problem is reduced somewhat as the inner diameter of the tube is increased relative to the outer diameter of the guide-wire.

The surface of the inner shaft can be treated to reduce the coefficient of friction of the surface moving against the guide-wire, to reduce the problem. The surface of the inner shaft can thus include a polymer coating such as Parylene C available from Para Tech Coating Inc. of Alisa Viejo, Calif. Parylene C is an organic polymer in which the repeat unit is a monochloro-substituted para-xylylene unit: —$CH_2(C_6H_3Cl)CH_2$—. Parylene C has a coefficient of dynamic friction value of 0.29, the coefficient of static friction has the same value. Reference for the coefficient of friction value and the polymer composition can be found in the product pamphlet "SCS Parylene Specifications and Properties" from Specialty Coating Systems, 7645 Woodland Drive, Indianapolis, Ind., 46278, or at www.scscoatincgs.com/parylene_knowledge/specifications.cfm. The coating can be applied to a maximum thickness of 0.00025" on the inside of the tube in order to limit the reduction in the inner diameter due to the presence of the coating, but a thicker coating could also be used, especially if the inner diameter of the sleeve were larger, at least at the tapered (distal end), say about 3 inches of the tapered end of the tube, inside and outside.

Characterization of the coating thickness can be accomplished by encapsulating the distal end of the sleeve in an acrylic or epoxy mounting resin, sectioning the sleeve at right angles to the tube axis of the sleeve, and then measuring the coating thickness using a microscope with a calibrated measuring overlay. Parylene C is a polymer based on repeating monomer units made of para-xylene, with a substitution of a chlorine atom for one of the aromatic hydrogens in the para-xylene monomer unit. Other parylene polymers are described below.

A preferred sleeve is likely to be one that can be used with monorail type of delivery system, such generally being considered superior for rapid exchanges while operating on a patient. Alternatively, an over-the-wire (OTW) type could be considered but is considered less likely to be as advantageous as a monorail type device.

The distal tip section 18 of the sleeve is of a metal or metal alloy that can be shaped to provide a suitably sharp leading edge for cutting or shaving a lesion as it is being crossed. Examples of such materials include, for example, nickel-titanium alloy (nitinol), stainless steel, a cobalt-chromium-molybdenum alloy, a titanium alloy or some other metal or alloy. Polymer and composite materials could also be considered for use to either coat the sleeve or for making the distal tip section.

The distal tip of the sleeve is tapered and of sufficient strength to cross the small channel initially traversed by the guide-wire. In crossing this channel, the sleeve tip may "shave" a thin layer of plaque that is highly fibrotic or even calcified in order to enlarge the channel.

The device can include a sleeve (a single tube) of unitary construction. There can be a sheath welded or otherwise joined to the sleeve upstream thereof, i.e. at a proximal location with respect to the sleeve at the tip section of the device. The sheath is generally more flexible than the sleeve to permit greater ease of movement over the guide-wire than if a unitary metal sleeve of equivalent length to the combined parts were used.

The inner lumen of the sleeve (i.e. surface of the interior through which a guide-wire is received) can be coated with a polymer or other material, or given a suitable surface treatment so as to decrease friction with the guide-wire.

A radio-opaque marker made, for example, of gold, platinum, iridium, palladium, rhodium, or a combination of these or similar materials can be placed at the distal tip of the sleeve with additional markers placed at regular intervals from the tip, e.g., spaced every 10 mm or so for total distance of 40 mm so that lesion length can be measured.

Photographs of the first embodiment sleeve are shown in FIGS. 2(*a*) and 2(*b*).

Figure 3:
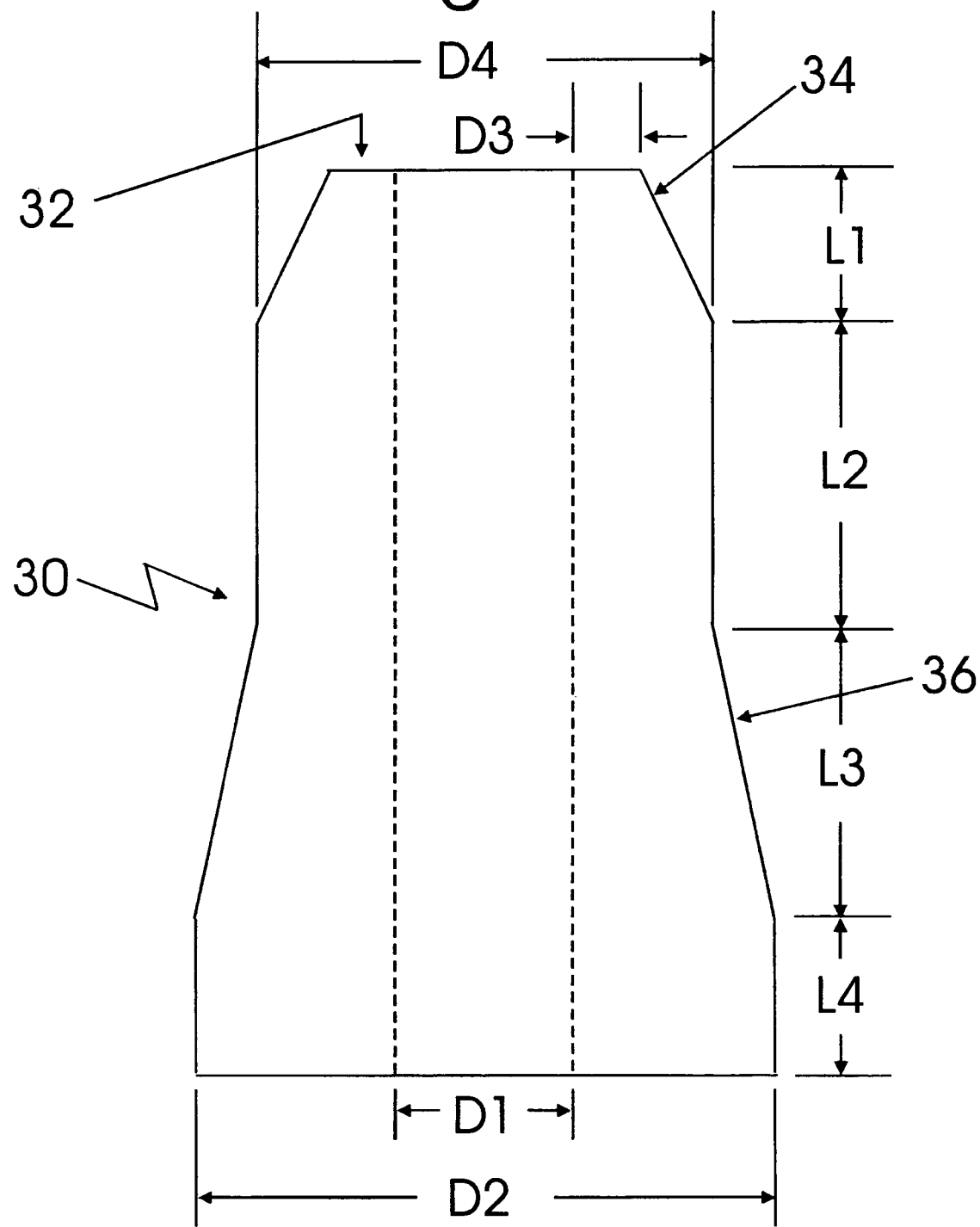
FIG. 3 is a second embodiment sleeve of the invention in longitudinal section.

A second embodiment sleeve 30 is shown in FIG. 3. The diameter, D1, of the guide-wire lumen is 0.017 inches and the maximum outer diameter D2 of the sleeve is 0.024 inches. The thickness, D3, of leading edge 32 is 0.001 inches, as with the first embodiment. The leading tapered surface 34 has a length, L1, of 0.100 inches. This is followed by an intermediate section of constant cross-section having an outer diameter, D4, of 0.022 inches and length, L2, of 12 inches. This is followed by a second tapered surface 36 having a length, L3, of 0.300 inches, followed by the proximal portion of constant cross-section having a length, L4, of 43 inches.

A third embodiment device 40 for use with a monorail delivery system, is illustrated in FIG. 4. In a monorail style catheter, the lumen for the guide-wire extends through only a distal portion of the catheter, typically from a distal tip aperture to a proximal aperture formed in the side wall of the catheter body. As the catheter is advanced over the pre-positioned guide-wire, the proximal end of the guide-wire will emerge from the side wall aperture such that the proximal portion of the guide-wire remains outside of the catheter body as the catheter is advanced to its desired operative site. The length of the catheter that must be passed over the guide-wire is lessened in the monorail type of arrangement making it generally easier for the operator to manually stabilize the guide-wire.

Sleeve 42 again includes nitinol tubing having an inner diameter D1 of 0.017±0.0005 inches and an outer diameter at its thickest point, D2, of 0.022±0.0005 inches. The outer diameter D3 of the distal tip of the sleeve is 0.019±0.0015 inches giving a thickness of the leading, or cutting edge of the sleeve of about 0.001 inches. The tapered surface 20 of the leading portion of the sleeve extends a distance, L1, of 0.120±0.050 inches upstream of the leading edge 12. The proximal portion 44 of sleeve extends longitudinal distance L2 11.4 cm (about 4.5 inches) upstream of the leading tapered portion so that the overall length of the sleeve is about 4.6 inches (about 11.7 cm).

The surface of the inner shaft of the tubing can have a coat 45 such as polymer coating e.g. a parylene polymer as described in connection with the first embodiment sleeve.

Sleeve 42 is secured at its proximal end 44 within the guide-wire lumen tube, sheath 46. As illustrated, proximal end 44 is suitably tapered for receipt within the interior passage of sheath 46, the members being affixed by suitable adhesive as may be deemed necessary. Guide-wire lumen tube 46 is of a polymeric tube such as that of coronary stent delivery balloon catheter available from Medtronic (Medtronic, Inc., Minneapolis, Minn., U.S.A.) Guide-wire lumen tube 46 has an outer diameter D4 of approximately 0.024 inches and an inner diameter D5 of approximately 0.018 inches. The polymeric tube is of a flexibility suitable for passage on a monorail guide-wire through the arterial system of a patient. In the illustrated prototype device, the proximal end sleeve 44 is received within the distal end of tube 46 into which it is snugly received. Guide-wire lumen tube 46 and a proximal portion of sleeve 42 are together received within outer casing tube 48. Outer casing tube 48, a polymeric tubing with an outer diameter of about 0.041 inches and an inner diameter of about 0.031 inches stiffens the device over the length of tube 46 and is connected at its proximal end 50 to pusher wire 52. Pusher wire 52 can be of stainless steel wire having an outer diameter of about 0.022 inches, stainless steel tubing, etc. Heat shrink tubing 54 is installed over the joint of the guide-wire lumen tube 46 and sleeve 42, over outer casing tube 48, and extending longitudinally beyond the distal end of tube 48 to directly contact the outer surface of sleeve 42. Heat shrink tubing 54 is a polymeric heat shrink material, e.g., polyethylene terephthalate (PET) having shrink temperature range is 85° C. to 190° C., with a typical shrinkage temperature of 150° C., melting point=235° C. Typical shrinkage is about 15% of diameter. The material can be sterilized by ethylene oxide or gamma radiation. The nominal wall thickness used for this prototype was 0.0005 inches and the inner diameter (before shrinking) was 0.043 inches+/−0.002 inches. The heat shrink tubing used for making the prototype was obtained from Advanced Polymers Inc., 29 Northwestern Drive, Salem, N.H. 03079-2838. Heat shrink tubing 54 or an equivalent element might be found to be unnecessary if sleeve 42 and casing tube 48 were adhered together with adhesive of sufficient strength and durability.

A heat shrink tubing (not illustrated) was applied over the outer surface of the sleeve 42, along its length, to reduce friction in the blood vessel. This heat shrink tubing was similar to that was used to fasten the outer casing tube 48 to sleeve 42, except that it had a pre-shrink diameter of 0.024 inch+/−0.001 inch, with a wall thickness of 0.0005 inch+/−0.0001 inch.

A radio-opaque marker 56 is situated at a convenient location, e.g., 5 mm upstream of the distal end of the sleeve, to aid use of the device by a surgeon. Guide-wire exit port 58 is adjacent the attachment point of the pusher wire, the length of the guide-wire lumen extending between distal end 12 and port 58.

A variation of the third embodiment device is shown in FIG. 4(a) in which heat shrink material 54' affixes pusher wire 52 and casing tube 48. Plastic handle 59 is illustrated schematically at the proximal end of the pusher wire.

The pusher wire and sleeve should be affixed relative to each to assure with sufficient strength that the pusher wire can be used to reliably advance the sleeve along the guide-wire. The heat shrink tubing of the prototype device could thus be replaced by polymer holder that encapsulates casing tubing 48 and the distal end of the pusher wire.

A fourth embodiment device 60, also contemplated for use with a monorail delivery system, is illustrated in FIG. 5. This embodiment is a simplified version of the prototype third embodiment. The dimensions and tapering of the leading or distal end 12 of the nitinol sleeve are similar to those of the FIG. 4 embodiment. The overall to length, L5, of the nitinol sleeve 62 is about 26 cm, the sleeve being affixed at its proximal end to the distal end of stainless steel pusher wire 64 by suitable attachment means. The length of overlap, L6, of the wire and sleeve is about 3.8 cm. In the illustrated embodiment the sleeve and pusher wire are affixed to each other by a solder joint. Sleeve 60 includes a pair of radio-opaque markers spaced 2 cm and 21.7 cm, respectively, upstream of the leading end of the sleeve. A stainless steel pusher wire having an outer diameter of about 0.015 inches may be suitable. The pusher wire is a suitable length for the intended purpose of the device, e.g., 127 cm, depending primarily on the location of the lesion to be treated.

The feasibility of the invention described herein has been established by the studies described further below, and it will be appreciated that optimal dimensions and materials can be developed by the skilled person given the teachings of this specification.

For example, the combination of the outer casing tube 48 and the guide-wire lumen tube 46 of the FIG. 4(a) embodiment could be replaced with one thicker polymer tube, which has an inner diameter of size such that it can be connected with sleeve 42 and provide an adequate size for easy guide wire sliding, and outer diameter to give it stiffness equivalent to the combination of the outer casing tube 48 and the guide-wire lumen tube 46.

It will be appreciated that each of the illustrated sleeves has an outer sidewall that is relatively free of cutting edges or other protuberances. The sleeve of the illustrated embodiments taken in cross-section presents an annulus, i.e., the wall defined between the surface of the lumen of the sleeve and the outer surface of the sleeve is defined by two concentric circles. In preferred embodiments, the tapered portion(s) of the sleeve makes up a relatively small proportion of the length of the sleeve, between zero (no tapered portion) up to about 20 percent of the length, but more typically less than about 10 percent, or less than about 5 percent the length of the sleeve. In the last such embodiment, the sleeve, being formed of a single piece of nitinol, is thus of unitary construction, has an annular cross-section over its entire length, and is of constant cross-section at its proximal end (or upstream end) for at least 95 percent of its length. In the FIG. 4 prototype embodiment, this specification it is the exposed proximal end of the sleeve which has a constant cross-section.

As mentioned above, a sleeve of the invention is typically nitinol, stainless steel, a cobalt-chromium-molybdenum alloy, a titanium alloy or some other metal or alloy, but it could be of a polymer or composite material. The material is preferably metal and is suitably flexible for delivery through the human blood vessels through which it must pass. The material of the prototypes described herein is a superelastic "nickel-titanium (nitinol)" alloy. "Superelasticity" is described in U.S. Pat. No. 6,824,560, which issued to Pelton on Nov. 20, 2004, and references cited therein. As described by Pelton, "pseudoelasticity" is the capacity of the nickel-titanium alloy to undergo large elastic strains on the order of 8 percent or more when stressed and to substantially fully recover all strain upon removal of the stress. Substantially full recovery is typically understood to be less than 0.5 percent unrecovered strain, also known as permanent set or amnesia. Pseudoelasticity can be further divided into two subcategories: "linear" pseudoelasticity and "non-linear" pseudoelasticity. "Non-linear" pseudoelasticity is sometimes used by those in the industry synonymously with "superelasticity." Linear pseudoelasticity results from cold working only. Non-linear pseudoelasticity results from cold working and subsequent heat treatment. Non-linear pseudoelasticity, in its idealized state, exhibits a relatively flat loading plateau in which a large amount of recoverable strain is possible with very little increase in stress. This flat plateau can be seen in the stress-strain hysteresis curve of the alloy. Linear pseudoelasticity exhibits no such flat plateau. Non-linear pseudoelasticity is known to occur due to a reversible phase transformation from austenite to martensite, the latter more precisely called "stress-induced martensite" (SIM). Linear pseudoelasticity has no such phase transformation associated with it. Further discussions of linear pseudoelasticity can be found in, for example, T. W. Duerig, et al., "Linear Superelasticity in Cold-Worked Ni—Ti," Engineering Aspects of Shape Memory Alloys, pp. 414-19 (1990).

The tapering of the nitinol tube was carried out on a centerless grinding machine.

Figure 6:
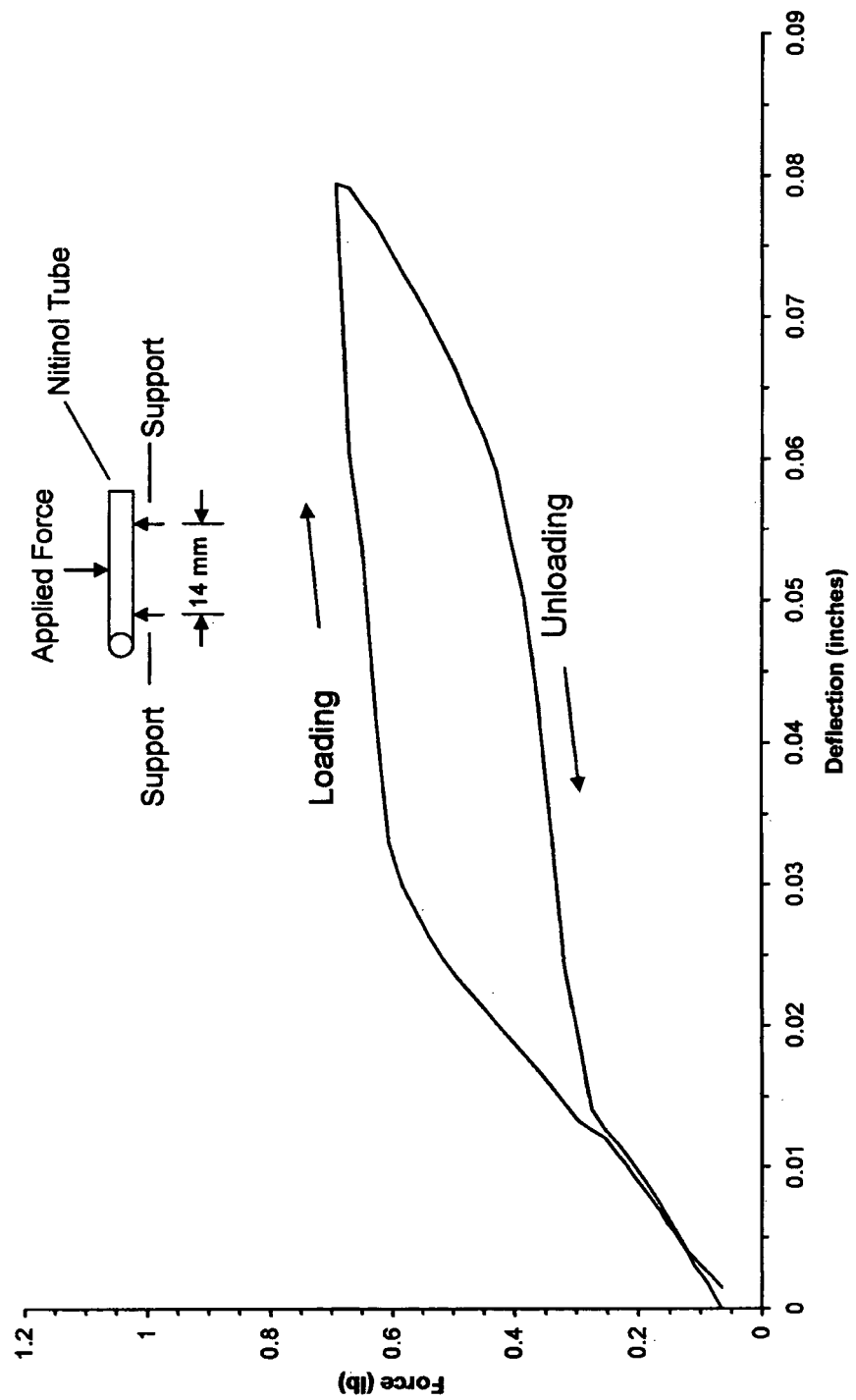
FIG. 6 shows the results obtained using a three point bending test of a nitinol tube used to manufacture a sleeve of the invention.
Figures 7A, 7B, 7C, 7D, 7E, 7F:
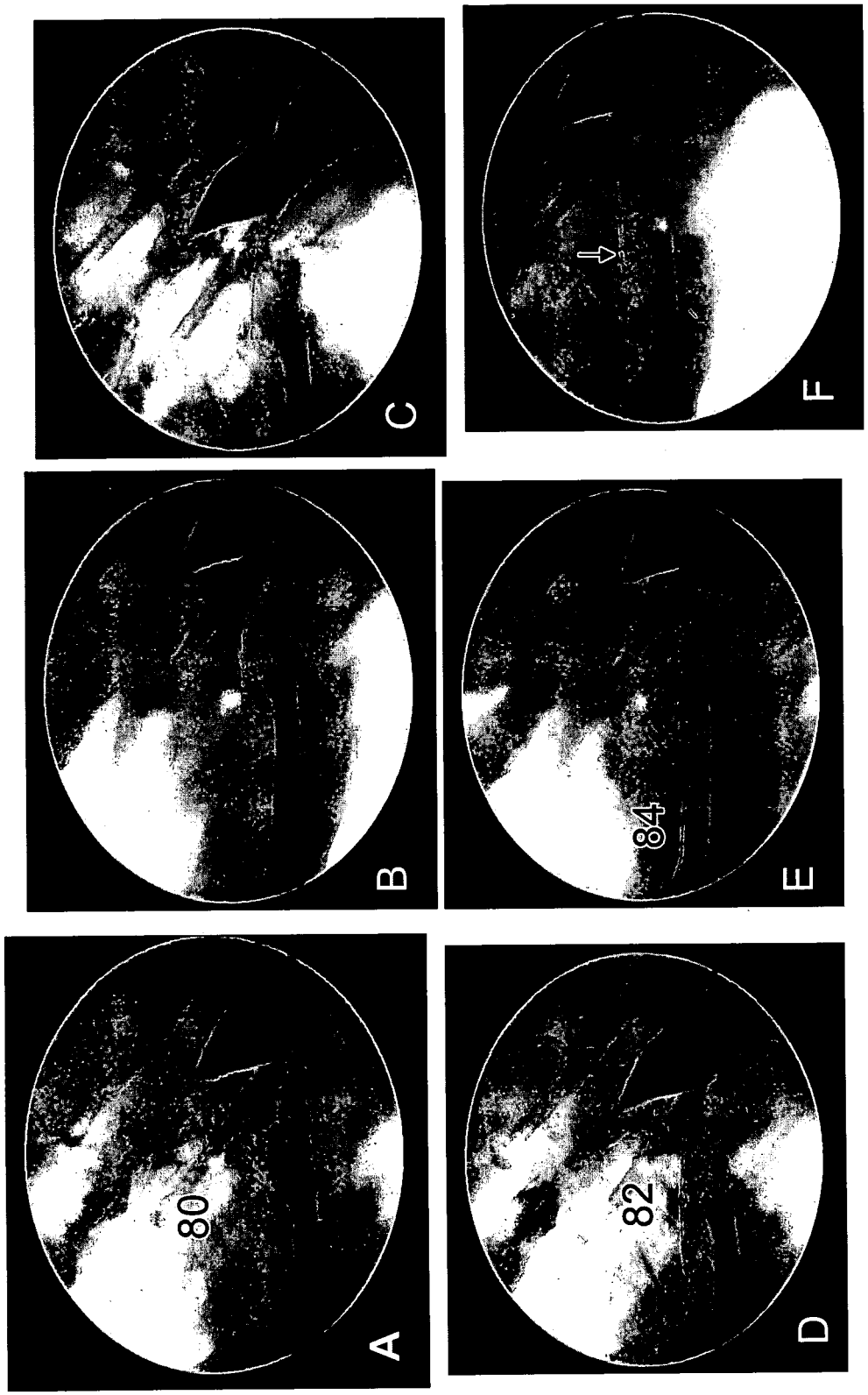
FIG. 7(a) is photograph of a femoral artery occlusion of a rabbit, as described in a first feasibility study. The occlusion is located between the two arrows.
FIG. 7(b) shows a guide-wire directed toward the beginning (proximal end) of the occlusion. The guide-wire, is indicated by the arrow.
FIG. 7(c) shows the guide-wire inserted into the occlusion, and having a balloon mounted thereon for support. The distal end of the balloon has a radio-opaque label, indicated by the arrow.
FIG. 7(d) shows the guide-wire crossing the occlusion.
FIG. 7(e) shows the guide-wire crossing the occlusion, but advanced distally further than in FIG. 7(d). The distal end of the wire is more radio-opaque than the following end of the wire.
FIG. 7(f) shows the extent to which the balloon can be advanced along the guide-wire prior to treatment of the occlusion in accordance with the present invention.
Figure 7G:
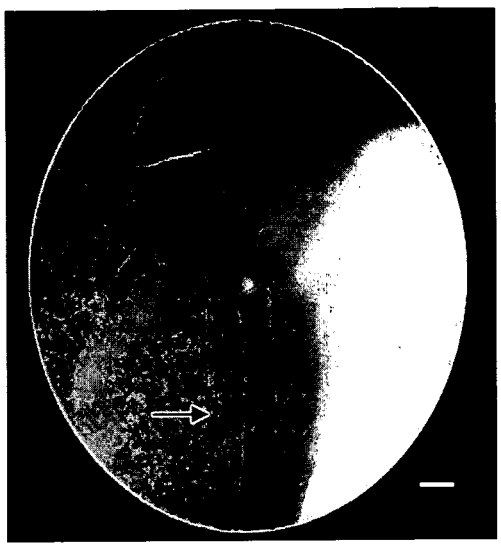
FIGS. 7(g) and 7(h) show a prototype sleeve of the present invention advanced to the distal end of the occlusion, the proximal end of the sleeve being indicated by the arrow, and the sleeve being slightly more radio-opaque than the guide-wire.
Figure 7H:
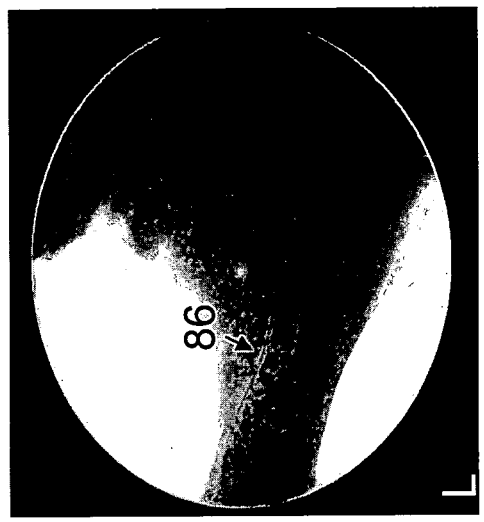
Figure 7I:
FIGS. 7(i) to 7(k) show the sleeve advanced through the occlusion to varying extents.
Figure 7J:
Figure 7K:
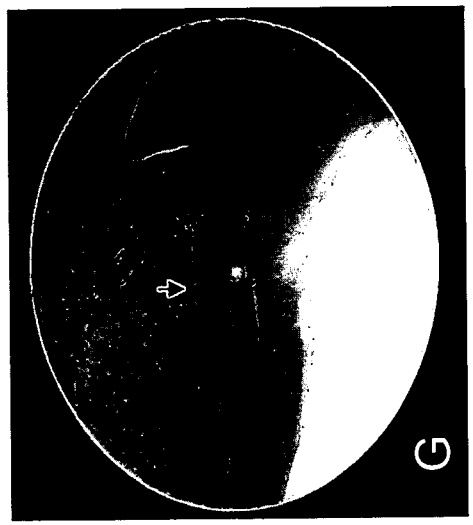
Figure 7L:
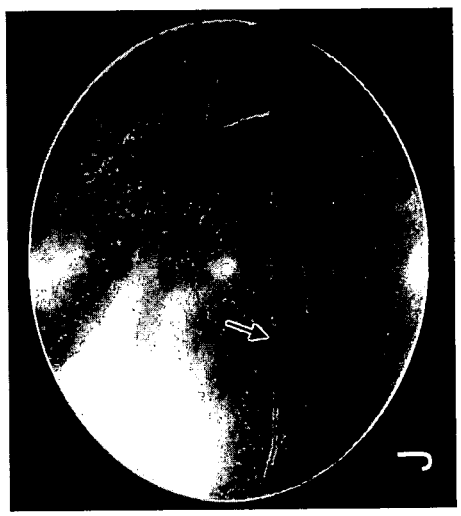
FIG. 7(l) shows a balloon advanced along the guide-wire across the occlusion subsequent to treatment of the occlusion in accordance with the present invention, the distal end of the balloon highlighted by the radio-opaque dot indicated by the arrow.

In the case of the third embodiment sleeve used here, a three-point bending test was conducted on the tubing used to produce the prototype, and the results are shown in FIG. 6. The bend span for the test was 14 mm, i.e., the supports for the sleeve were spaced 14 mm apart. The nitinol tube as purchased was received as straight, superelastic nitinol tubing with a loading plateau stress of 60,000 psi minimum, an ultimate tensile strength of 165,000 psi minimum, a permanent set after 8% elongation of 0.5% maximum, and a minimum elongation of 10.0%, all measured in a temperature range of 20° C. to 25° C. The nitinol tube was subject to heat treatment at 380° C. for 30 minutes. It is expected that acceptable flexibility of the metal is achieved when the $A_f$ temperature (austenite transformation finish temperature) of the metal is in the range of 35° C. to 45° C. While the $A_f$ temperature of the nitinol tube of the third embodiment was measured to be about 35° C., it is thought that an $A_f$ temperature slightly above this would may be found to be closer to optimal.

Another possible metal for a sleeve of the invention is NiTiCu alloy, described in U.S. Pat. No. 5,683,245, which issued on Nov. 4, 1997 to Sachdeva et al. Such a NiTiCu alloy may have less tolerance variability in the $A_f$ temperature than nitinol, and thus the possible ensuing advantage of less stiffness variability between material lots. The loading and unloading stress/force plateaus are closer together for NiTiCu than for NiTi (i.e., less mechanical hysteresis), which may also provide reduced stiffness relative to NiTi while still maintaining full superelasticity.

As mentioned above, it may be found advantageous with the sleeve of the invention to coat the surface of the guide-wire lumen of the sleeve with a polymer to ease travel of the sleeve over the guide-wire. Parylene C, described above, is a particular member of parylene polymers described, for example in U.S. Pat. No. 5,075,014, which issued to Pile on Dec. 24, 1991, and U.S. Pat. No. 5,879,808, which issued to Wary et al. on Mar. 9, 1999. The parlyene polymer is advantageously applied by a vapor deposition method, as described in U.S. Pat. No. 5,879,808.

Feasibility Studies

Figure 8:
FIGS. 8(a) and 8(b) are angiograms obtained after removal of the balloon and guide-wire.
Figure 8:
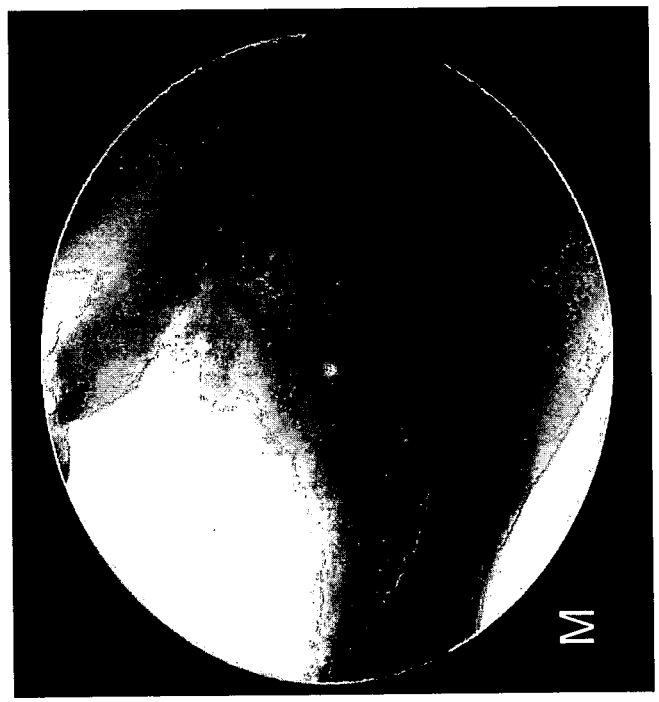
Figure 9B:
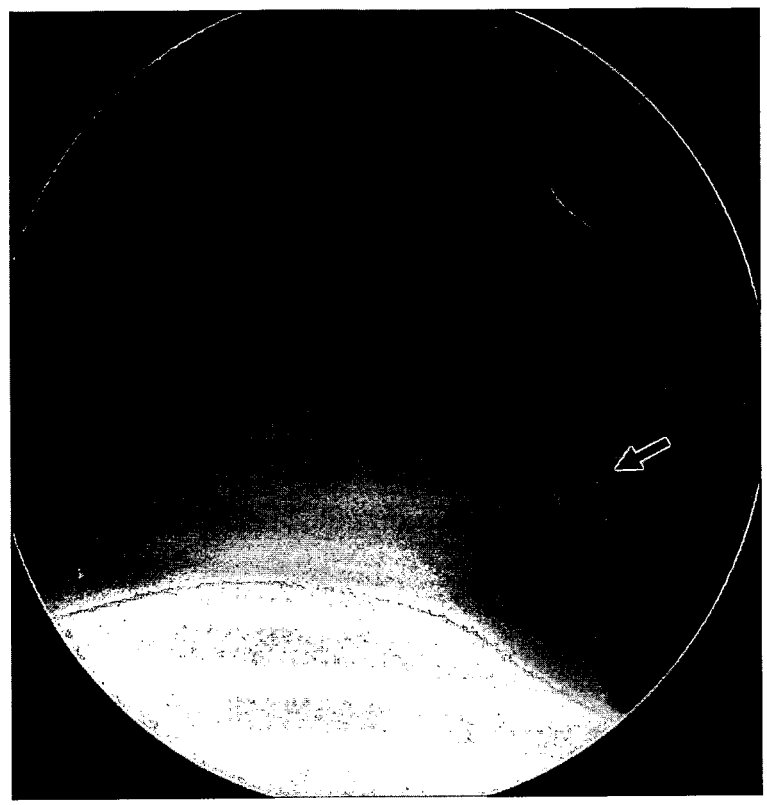
FIG. 9(b) shows a wisdom guide-wire directed toward the beginning (proximal end) of the occlusion. The distal tip of the wisdom guide-wire, is indicated by the arrow.
Figure 9A:
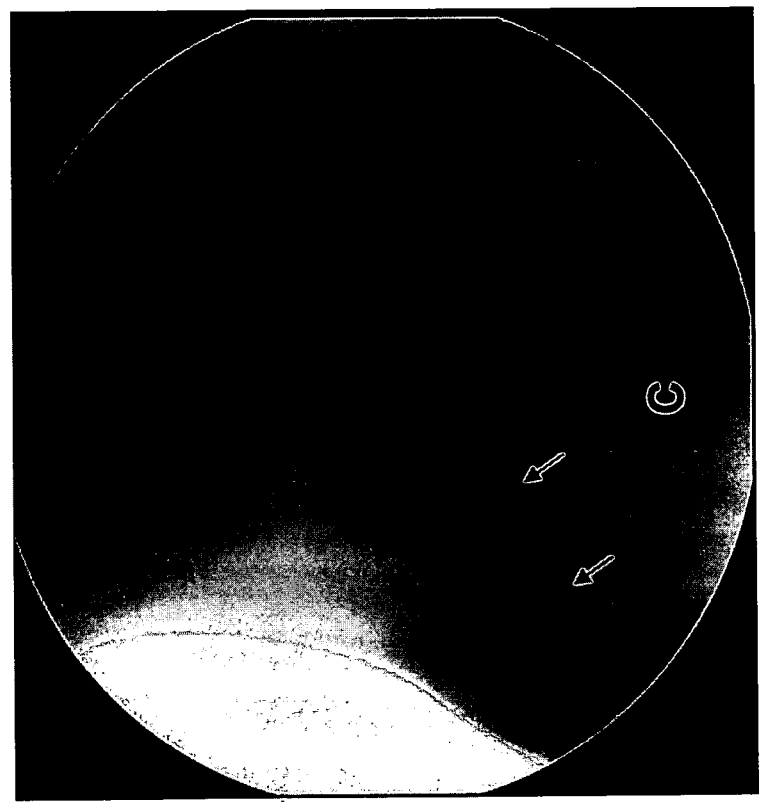
FIG. 9(a) is an angiogram of a femoral artery occlusion of a rabbit at the beginning of a second feasibility study. The occlusion is located between the two arrows.
Figure 9D:
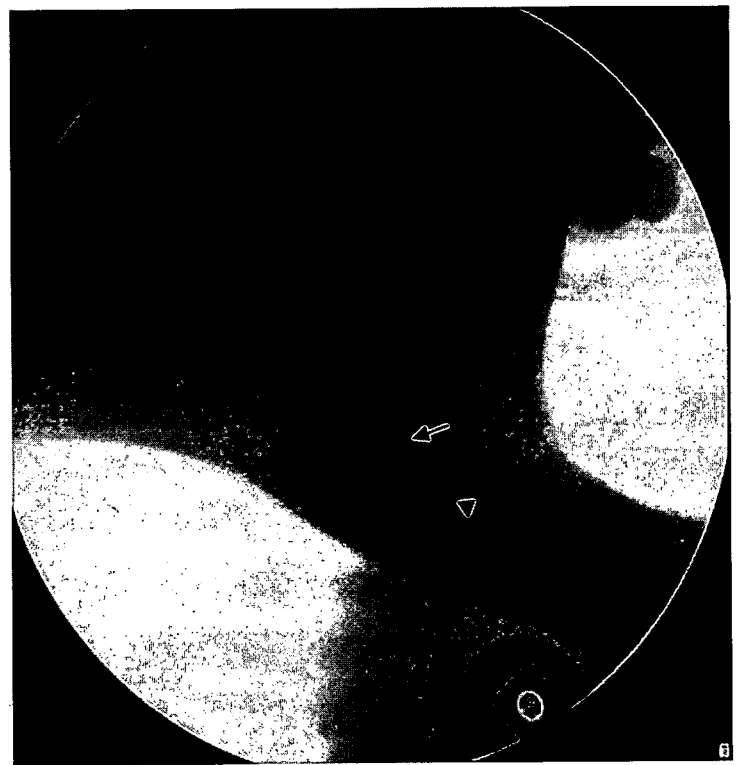
FIG. 9(d) shows the occlusion after the angioplasty balloon catheter has been removed and the guide-wire sleeve has been advanced therethrough. The guide-wire is more radio-opaque at the distal end of the wire (shown as arrowhead). The sleeve is slightly more radio-opaque than the less-radio-opaque parts of the underlying guide-wire and the distal tip of the sleeve is indicated by an arrow.
Figure 9C:
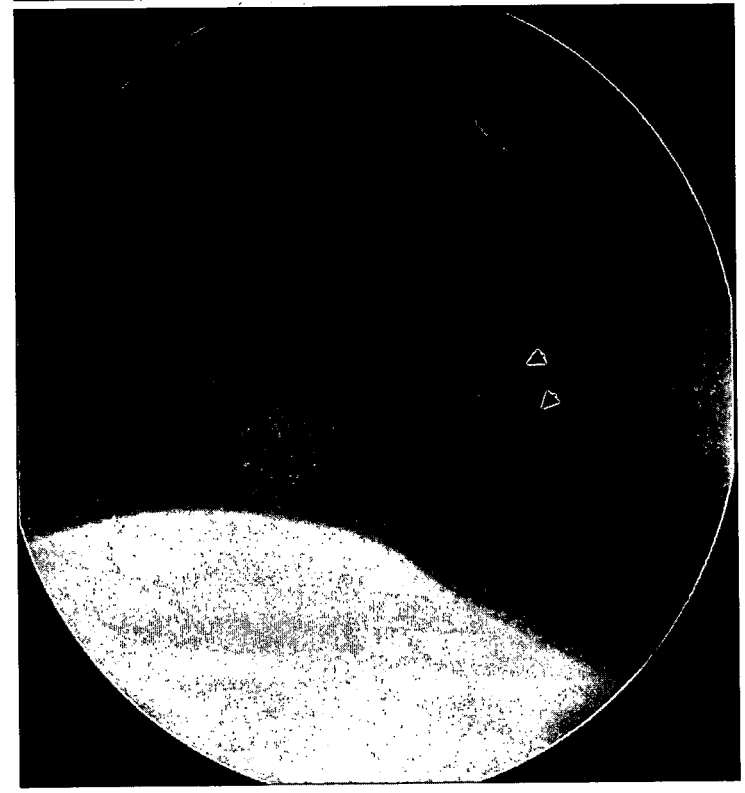
FIG. 9(c) shows the wisdom guide-wire after crossing an occlusion that an angioplasty balloon catheter (two balloon markers are indicated by arrows) was found not possible to cross.

Studies were carried out to establish the feasibility of improving the outcome of lesion crossing using the first and third embodiments of the invention. Studies 1 and 2 involved the use of the FIG. 1 embodiment, while Study 3 involved the use of the FIG. 8 embodiment.

Study 1

A rabbit femoral artery occlusion model has been developed as previously described (35). In a 9 week old occlusion, a 0.014" angioplasty guide-wire [ATW, Cordis] was positioned in the guide-wire port of a conventional 1.5 mm diameter, 15 mm length over-the-wire balloon angioplasty catheter and directed to the beginning of the occlusion 80, FIGS. 7(*a*) and (*b*). The guide-wire 82 was then successfully advanced across the total occlusion into the distal artery 84, FIGS. 7(*c*) to 7(*e*). A vigorous attempt to advance the balloon catheter across the total occlusion was unsuccessful, FIG. 7(*f*). The guide-wire and catheter were removed from the animal and the guide-wire was inserted into a nitinol prototype sleeve of a design described above, so that it extended beyond the sleeve. The guide-wire-sleeve was directed to the beginning of the chronic total occlusion and the guide-wire was successfully advanced across the total occlusion into the distal artery, FIGS. 7(*g*) and (*h*). The sleeve was then advanced over the guide-wire across the total occlusion, FIGS. 7(*i*) to 7(*k*). The guide-wire-sleeve was removed. An angiogram demonstrated a larger channel across the occluded arterial segment. The guide-wire was then placed back inside the angioplasty balloon catheter and directed into the occluded artery. The guide-wire was advanced across the occlusion into the distal artery. The angioplasty balloon catheter 86 was then easily advanced over the guide-wire into the distal artery, FIG. 7(*l*). An angiogram was obtained, FIGS. 8(*a*) and 8(*b*) which showed flow through the occluded artery and confirmed the channel across the occlusion was larger than before the sleeve was used and there was no evidence of dissection. The animal was sacrificed and the artery was removed. Histological examination confirmed that an open channel through the occlusion had been successfully created.

Study 2

In this study, a nitinol tube having a ¼ of a thousandth of an inch (6.35 microns) polymer coating, Parylene C (Para Tech Coating Inc, Alisa Viejo, Calif.) was used. The coating was on the inside and outside of the sleeve tube for a couple of inches at the leading (distal) end of the tube. The interior coating gradually diminished in thickness along the length of the tube in the proximal direction and had maximal thickness near the distal end of the tube. Parylene C was found to adhere to the nitinol (tubular) substrate. The coating is not hydroscopic in itself, but it can glide over a water layer adsorbed onto the guide-wire polymer surface layer.

A 12 week-old occlusion was established in a rabbit femoral artery, the occlusion being between the two arrows of FIG. 9(*a*). A 0.014" angioplasty guide-wire [Wisdom, Cordis] was positioned in the guide-wire port of a conventional 1.5 mm diameter, 12 mm length rapid exchange balloon angioplasty catheter (Maverick, Boston Scientific) and directed to the beginning, proximal end of the occlusion, indicated by the arrow in FIG. 9(*b*). The guide-wire was then successfully advanced across the total occlusion into the distal artery (FIG. 9(*c*)). A vigorous attempt to advance the balloon catheter across the total occlusion was unsuccessful (FIG. 9(*c*)). The guide-wire and catheter were removed from the animal and the guide-wire was inserted into a prototype sleeve of a design described above that was coated with 0.00025" parylene C polymer, so that the guide-wire extended beyond the sleeve. The guide-wire-sleeve was directed to the beginning of the chronic total occlusion and the guide-wire was successfully advanced across the total occlusion into the distal artery. The sleeve was then advanced over the guide-wire across the total occlusion, the distal end of the sleeve being indicated by the arrow in FIG. 9(*d*) and the distal end of the guide-wire being indicated by the arrowhead. The guide-wire-sleeve was removed. An angiogram demonstrated a larger channel across the occluded arterial segment. The guide-wire was then placed back inside the angioplasty balloon catheter and directed into the occluded artery. The guide-wire was advanced across the occlusion into the distal artery. The angioplasty balloon catheter was then advanced over the guide-wire into the distal artery as indicated by the arrows in FIG. 9(*e*). After removal of the guide-wire and the angioplasty balloon catheter, an angiogram showed flow through the occluded artery and confirmed the channel across the occlusion was larger than prior to the procedure, without evidence of dissection (FIG. 4(f)). The animal was sacrificed and the artery was removed.

Histological examination confirmed that an open channel through the occlusion had been successfully created. FIGS. 10(a)-(e) show the histology of the chronic total occluded femoral artery of the second feasibility study after crossing with the guide-wire, the sleeve, and the angioplasty balloon catheter. In the figures can be seen the media 90, arterial lumen 92, intima 94. FIG. 10(a) shows the femoral artery immediately proximal to the occlusion. FIGS. 10(b), (c) and (d) are of the proximal, mid and distal parts of the occluded artery, respectively, and FIG. 10(e) is of the femoral artery immediately distal to the occlusion. The internal elastic lamina is indicated by arrows 96. Within the occlusion, the lumen is patent as a result of the passage of the guide-wire and angioplasty balloon therethrough. There is no apparent damage to the medial layer of the vessel wall as a result of the procedure;

Study 3

Figure 11:
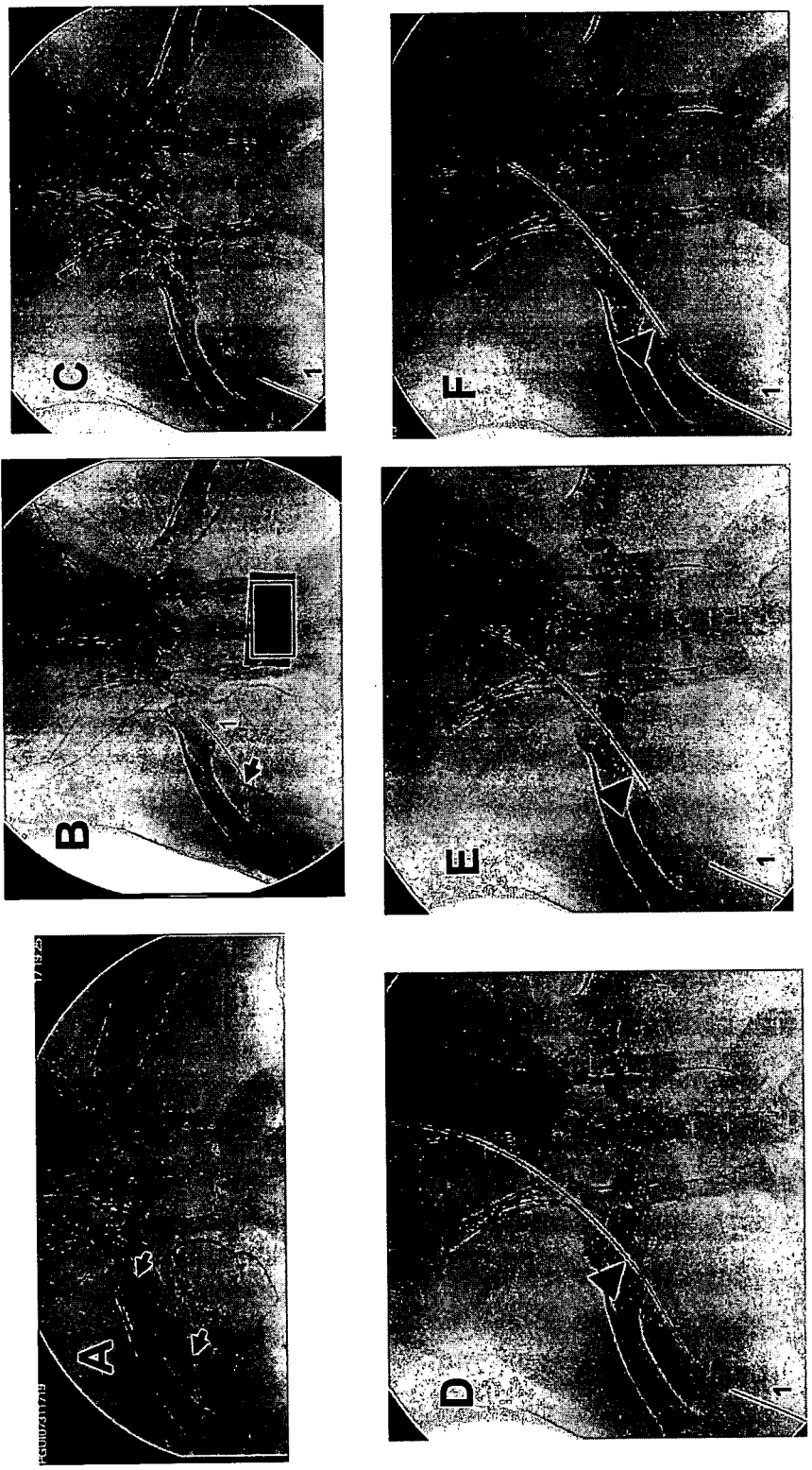
FIGS. 11(a) to 11(j) are angiograms showing results obtained in a third feasibility study.

A third study was carried out, according to the procedure of the second study but using the FIG. 4 embodiment device. Results obtained are shown in FIGS. 11(a) to 11(j). FIG. 11(a) is an angiogram showing an eight-month-old right femoral artery occlusion of a rabbit (between two arrows) with extensive collaterals to distal femoral artery beyond occlusion. The left femoral artery is widely patent. FIG. 11(b) shows the advancement of a 0.014 inch guide wire to near the end of the occlusion, indicated by the arrow. The radio-opaque tip of the guide wire is indicated by the numeral "1" in this and all subsequent angiograms. FIG. 11(c) shows that the guide wire has crossed the occluded segment and has been advanced into the distal artery. A 2.0 mm diameter over-the-wire balloon catheter could not be advanced across the occluded segment. FIG. 11(d) shows the sleeve advanced to beginning of occlusion. The radio-opaque marker at the distal end of the sleeve is indicated by arrow-head in this and all subsequent figures. FIGS. 11(e) to 11(h) show progression of the sleeve across the occluded segment. FIG. 11(i) shows that the sleeve has completely crossed the occlusion into the distal vessel. FIG. 11(j) is an angiogram taken after removal of the guide-wire and guide-sheath showing reconstitution of the occluded segment (between two arrows). There was also some spasm evident in the right iliac artery.

While the foregoing studies establish the feasibility of the invention, it is thought that a sleeve of slightly more flexibility than that of the FIG. 4 embodiment device may achieve more optimal results.

REFERENCES

1) American Heart Association. Heart Disease and Stroke Statistics-2004 Update. Dallas, Tex.: American Heart Association; 2003
2) Ivanhoe R J, Weintraub W S, Douglas JS, et al. Percutaneous transluminal coronary angioplasty of chronic total occlusions: primary success, restenosis, and long-term clinical follow-up. Circulation 1992; 85:106-115
3) Stone G W, Rutherford B D, McConahay D R, Johnson W L Jr, Giorgi L V, Ligon R W, Hartzler G O. Procedural outcome of angioplasty for total coronary artery occlusion: an analysis of 971 lesions in 905 patients. J Am Coll Cardiol 1990; 15:849-56
4) Bell M R, Berger P B, Bresnahan J F, et al. Initial and long-term outcome of 354 patients after coronary balloon angioplasty of total coronary artery occlusions. Circulation 1992; 85:1003-11
5) Lefevre T, Louvard Y, Loubeyre C, et al. A randomized study comparing two guidewire strategies for angioplasty of chronic total coronary occlusion. Am J Cardiol 2000; 85:1144-7.
6) Kahler J, Koster R, Brockhoff C, et al. Initial experience with a hydrophilic-coated guidewire for recanalization of chronic coronary occlusions. Cathet Cardiovasc Interven 2000; 49:45-50
7) Puma J A, Sketch M H, Tcheng J E, et al. Percutaneous revascularization of chronic coronary occlusions—an overview. J Am Coll Cardiol 1995; 26:1-11
8) Kahn J K. Angiographic suitability for catheter revascularization of total coronary occlusions in patients from a community hospital setting. *Am Heart J* 1993; 126: 561-564.
9) Baim D S, Ignatius E J. Use of coronary angioplasty: Results of a current survey. Am J Cardiol 1988; 61:3G-8G
10) Noguchi T, Miyazaki S, Mor I, Daikoku S, Goto Y, Nonogi H. Percutaneous transluminal coronary angioplasty of chronic total occlusions: determinants of primary success and long-term outcome. Cathet Cardiovasc Intervent 2000; 49:258-264
11) Ivanhoe R J, Weintraub W S, Douglas J S, et al. Percutaneous transluminal coronary angioplasty of chronic total occlusions: primary success, restenosis, and long-term clinical follow-up. Circulation 1992; 85:106-115
12) Stone G W, Kandzari D E, Mehran R, Colombo A, Schwartz R S, Bailey S, Moussa I, Teirstein P S, Dangas G, Baim D S, Selmon M, Strauss B H, Tamai H, Suzuki T, Mitsudo K, Katoh O, Cox D A, Hoye A, Mintz G S, Grube E, Cannon L A, Reifart N J, Reisman M, Abizaid A, Moses J W, Leon M B, Serruys P W. Percutaneous Recanalization of Chronically Occluded Coronary Arteries: A Consensus Document. Part 1. Circulation 2005; 112(15):2364-72
13) Dzavik V, Beanlands D S, Davies R F, Leddy D, Marquis J-F, Teo K K, Ruddy T D, Burton J R, Humen D P. Effects of late percutaneous transluminal coronary angioplasty of an occluded infarct-related coronary artery on left ventricular function in patients with a recent (<6 weeks) Q-wave acute myocardial infarction (Total Occlusion post-Myocardial Infarction Intervention Study [TOMIIS]—A pilot study. Am J Cardiol 1994; 73:856-61
14) Pizzetti G, Belotti G, Margonato A, Cappelletti A, Chierchia S. Coronary recanalization by elective angioplasty prevents ventricular dilatation after anterior myocardial infarction. J Am Coll Cardiol 1996; 28:837-45
15) Sirnes P A. Myreng Y. Molstad P. Bonarjee V. Golf S. Improvement in left ventricular ejection fraction and wall motion after successful recanalization of chronic coronary occlusions. Eur Heart J 1998; 19:273-81
16) Danchin N. Angioi M. Cador R. Tricoche O. Dibon O. Juilliere Y. Cuilliere M. Cherrier F. Effect of late percutaneous angioplastic recanalization of total coronary artery occlusion on left ventricular remodeling, ejection fraction, and regional wall motion. Am J Cardiol 1996; 78:729-35.
17) Lamas G A, Flaker G C, Mitchell G, et al. for the Survival Ventricular Enlargement Investigators. Effect of infarct artery patency on prognosis after acute myocardial infarction. Circulation 1995; 92:1101-1109.
18) Suero J A, Marso S P, Jones PG, et al. Procedural outcomes and long-term survival among patients undergoing percutaneous coronary intervention of a chronic total occlusion in native coronary arteries: a 20-year experience. J Am Coll Cardiol 2001; 38:409-14

19) Ramanathan K, Gao M, Nogareda G J, et al. Successful percutaneous recanalization of a non-acute occluded coronary artery predicts clinical outcomes and survival. Circulation 2001; 104:415A (abstract).

20) Srinivas V S, Borrks M M, Detre K M, et al. Contemporary percutaneous coronary intervention versus balloon angioplasty for multivessel coronary artery disease. A comparison of the National Heart, Lung, and Blood Institute Dynamic Registry and the Bypass Angioplasty Revascularization Investigation (BARI) study. Circulation 2002; 106:1627-1633

21) King S B, Lembo N J, Weintraub W S, et al., for the Emory Angioplasty versus Surgery Trial Investigators. A randomized trial comparing coronary angioplasty with coronary bypass surgery. N Engl J Med 1994; 331: 1044-1050.

22) Stone G W, Rutherford B D, McConahay D R, Johnson W L Jr, Giorgi L V, Ligon R W, Hartzler G O. Procedural outcome of angioplasty for total coronary artery occlusion: an analysis of 971 lesions in 905 patients. J Am Coll Cardiol 1990; 15:849-56

23) Tan W, Sulke A N, Taub N A, et al. Determinants of success of coronary angioplasty in patients with a chronic total occlusion: a multiple logistic regression model to improve selection of patients. Br Heart J 1993; 70:126-31

24) Safian R D, McCabe C H, Sipperly M E, et al. Initial success and long-term follow-up of percutaneous transluminal coronary angioplasty in chronic total occlusions versus conventional stenoses. Am J Cardiol 1988; 61:23 G-28G 25) Serruys P W, Umans V, Heyndrickx G R, et al. Elective PTCA of totally occluded coronary arteries not associated with acute myocardial infarction: short term and long-term results. Eur Heart J 1985; 6:2-12

26) Bilodeau L, Fretz E B, Taeymans Y, Koolen J, Taylor K, Hilton D J. Novel use of a high-energy excimer laser catheter for calcified and complex coronary artery lesions. Catheter Cardiovasc Interv. 2004 June; 62(2): 155-61.

27) Contreras G, Cieza T, Hardy N, Bilodeau L. Uncrossable coronary obstruction treated by the new laser guidewire. J Invasive Cardiol. 2005 October; 17(10): 560-2.

28) Srivatsa S S, Edwards W D, Boos C M, Grill D E, Sangiorgi G M, Garratt K N, Schwartz R S, Holmes D R Jr. Histologic correlates of angiographic chronic total coronary artery occlusions: influence of occlusion duration on neovascular channel patterns and intimal plaque composition. J Am Coll Cardiol 1997; 29:955-63

29) Meier B. Chronic Total Occlusion. In: Textbook of Interventional Cardiology. Editior: E. Topol. W.B. Saunders, Philadelphia 1994:318-338

30) Bartos F, Ledvina M. Collagen, elastin, and desmosines in three layers of bovine aortae of different ages. Exp Gerontol 1979; 14:21-26

31) Hosoda Y, Kawano K, Yamasawa F, Ishii T, Shibata T, Inayama S. Age dependent changes of collagen and elastin content in human aorta and pulmonary artery. Angiology 1984; 35:615-21

32) Mayne R. Collagenous proteins of blood vessels. Arteriosclerosis 1986; 6:585-593

33) Katsuda S, Okada Y, Minamoto T, Oda Y, Matsui Y, Nakanishi I. Collagens in human atherosclerosis: immunohistochemical analysis using collagen type-specific antibodies. Arterioscler Thromb 1992; 12:494-502

34) Tsuchikane E, Katoh O, Shimogami M, Ito T, Ehara M, Sato H, Matsubara T, Suzuki T. First clinical experience of a novel penetration catheter for patients with severe coronary artery stenosis. Catheter Cardiovasc Interv 2005; 65(3):368-73.

35) Strauss B H, Goldman L, Nili N, Butany J, Jackson Z S, Segev A, Eskandarian M R, Sparkes J, Virmani R. Collagenase plaque digestion for facilitating guidewire crossing in chronic total arterial occlusions. Circulation. 2003; 108:1259-62.

The contents of all documents cited in this specification are incorporated herein by reference, and the applicants reserve the right to incorporate such contents directly into the specification.

The invention claimed is:

1. A dilation device for treatment of a mammalian vessel having an occlusion, the device comprising:
   an elongated hollow sleeve having a distal end and a proximal end, and a lumen configured for receipt of a guide-wire therethrough, wherein:
   the sleeve at least partially comprises a metal; and wherein the distal end is configured for dilating a channel containing the guide-wire primarily by wedging apart and thereby outwardly compressing portions of said occlusion surrounding the guide-wire as said distal end is advanced over the guide-wire and at least partially through said occlusion, wherein the sleeve is a single piece of metal of unitary construction.

2. The device of claim 1, wherein the lumen of the sleeve has a maximum diameter of 0.03 inches.

3. The device of claim 2 wherein a radial distance between a surface of the lumen and an outer surface of the sleeve is between 0.004 and 0.007 inches.

4. The device of claim 3 wherein the sleeve is of a flexible metal.

5. The device of claim 4 wherein said metal is superelastic.

6. The device of claim 2, wherein the lumen of the sleeve has a diameter which is about 0.015 to about 0.018 inches.

7. The device of claim 1, further comprising a pusher wire connected at a proximal end of the sleeve to permit use of the device with a monorail delivery system.

8. The device of claim 7 wherein the sleeve has a length up to about 26 cm.

9. The device of claim 7 wherein the pusher wire has a length of at least about 32 cm.

10. The device of claim 7 wherein the sleeve further defines a guide-wire exit port at a proximal end of the lumen.

11. The device of claim 1 wherein a metal surface of the lumen has a coating to lower friction between the guide-wire and the metal surface of the lumen.

12. The device of claim 11, wherein said coating is parylene C.

13. The device of claim 1 wherein the distal end defines a distal tip that comprises a polymer.

14. The device of claim 1, wherein the distal end defines a distal tip providing a leading edge and having an outer surface, and wherein the outer surface of the distal tip forms a truncated cone extending from the leading edge up to at least about 0.15 inches proximal of the leading edge.

15. A sleeve for installation on a guide wire inserted through a mammalian vessel having an occlusion therein, the sleeve consisting essentially of:
   a hollow tip located at a distal end of the sleeve for passage of the wire therethrough, wherein:
   the tip provides a leading edge; and a smooth outer surface extends longitudinally from said leading edge, the outer surface shaped to primarily operate as a wedge to force an occlusion surface in abutment with the guidewire radially outwardly as the sleeve is advanced through the occlusion through which the wire has been inserted.

16. The sleeve of claim 15 wherein at least an interior distal end of the hollow tip is coated with a polymer, wherein the polymer is preferably an organic polymer, and optionally, wherein the polymer encapsulates the distal end of the sleeve and has a repeat unit of —$CH_2(C_6H_3Cl)CH_2$—, with a coefficient of dynamic friction value of 0.29 or greater, and a coefficient of static friction having at least the same value.

17. The device of claim 15 wherein the distal tip comprises a polymer.

18. A method of traversing an occlusion of an animal vessel, the method comprising:
inserting a guide wire into the vessel and at least partially through the occlusion to create a channel at least partially through the occlusion;
passing a hollow elongated sleeve, having a tapered distal tip, along the guide wire; and
advancing the sleeve into the occlusion so as to force material of said occlusion outwardly from the guide-wire to thereby dilate the channel primarily by wedging without substantial removal of material from said occlusion.

19. The method of claim 18, wherein the sleeve includes an outer surface trailing behind a leading edge, and wherein said outer surface cants radially outwardly from the leading edge to force a surface of the occlusion in abutment therewith outwardly as the sleeve is forced into the occlusion.

20. The method of claim 18, further comprising the use of a monorail delivery system wherein a pusher wire is connected at a proximal end of the sleeve for advancing the sleeve along the guide-wire and into the occlusion.

21. The method of claim 18, wherein the vessel is a coronary artery.

22. The method of claim 18, wherein the vessel is selected from the group consisting of an iliac artery, a femoral artery, a popliteal artery, a renal artery, a carotid artery, a vertebral artery, a ureter, a fallopian tube and a bile duct.

23. The method of claim 18, wherein the vessel is a peripheral artery.

24. A device for treatment of a mammalian vessel having an occlusion crossable by a guide-wire, the device comprising:
an elongated hollow smooth sleeve having a distal end and a proximal end and defining a lumen therethrough, the lumen having a diameter of about 0.015 to 0.018 inches for receipt of the guide-wire therethrough, the distal end being tapered and shaped to operate as a wedge to spread apart surrounding portions of said occlusion as said distal end is advanced over the guide-wire through said occlusion.

25. A kit for treatment of a mammalian vessel having an occlusion, the kit comprising:
a guide-wire having a diameter for inserting into the vessel and advancing at least partially across the occlusion; and
an elongated hollow smooth sleeve having a distal end and a proximal end, and defining a lumen for fitting receipt of the guide-wire therethrough, the lumen having a diameter which is about 0.001 to about 0.004 inches greater than the diameter of the guide-wire,
the distal end providing a tapered distal tip that is shaped to operate as a wedge to spread apart surrounding portions of said occlusion as said distal end is advanced over the guide-wire through said occlusion.

26. A device for use with a monorail delivery system for treatment of a mammalian vessel having an occlusion, the device comprising:
an elongated hollow sleeve having a distal end and a proximal end, the sleeve having a length up to about 26 cm, the sleeve defining a lumen for receipt of a guide-wire therethrough, the sleeve further defining a guide-wire exit port proximal from the distal end; and
a pusher wire operatively coupled about a proximal end of the sleeve; wherein
the distal end of the sleeve provides a tapered distal tip that is shaped to operate as a wedge to spread apart surrounding portions of said occlusion crossed by the guide-wire as said distal end is advanced over the guide-wire through said occlusion.

27. A method of traversing an occlusion of an animal vessel, the method comprising:
inserting a guide wire into the vessel and at least partially through the occlusion to create a channel at least partially through the occlusion;
passing a hollow elongated sleeve, having a tapered distal tip, along the guide wire; and
advancing the sleeve into the occlusion so as to dilate a channel containing the guide wire primarily by forcing said occlusion radially outwardly from the guide-wire.

28. A kit for treatment of a mammalian vessel having an occlusion, the kit comprising:
a guide-wire having a diameter for inserting into the vessel and advancing at least partially across the occlusion; and
an elongated hollow smooth sleeve having a distal end and a proximal end, and defining a lumen for receipt of the guide-wire therethrough, the guide-wire diameter being at least 78 percent of a diameter of the lumen,
the distal end providing a tapered distal tip that is shaped to operate as a wedge to spread apart surrounding portions of said occlusion as said distal end is advanced over the guide-wire through said occlusion.

* * * * *